(12) United States Patent
Fischer

(10) Patent No.: US 7,635,573 B2
(45) Date of Patent: *Dec. 22, 2009

(54) MASS SPECTROSCOPIC METHOD FOR COMPARING PROTEIN LEVELS IN TWO OR MORE SAMPLES

(75) Inventor: Steven M. Fischer, Hayward, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 419 days.

This patent is subject to a terminal disclaimer.

(21) Appl. No.: 11/317,993

(22) Filed: Dec. 22, 2005

(65) Prior Publication Data

US 2006/0134723 A1 Jun. 22, 2006

Related U.S. Application Data

(63) Continuation of application No. 10/341,310, filed on Jan. 13, 2003, now Pat. No. 7,422,865.

(51) Int. Cl.
*C12Q 1/37* (2006.01)
*C07K 1/00* (2006.01)
*C07K 17/06* (2006.01)
*C07K 17/08* (2006.01)

(52) U.S. Cl. .................. 435/23; 530/402; 530/412; 530/815; 530/816

(58) Field of Classification Search ............. None
See application file for complete search history.

(56) References Cited

U.S. PATENT DOCUMENTS

| | | | |
|---|---|---|---|
| 5,240,859 A | 8/1993 | Aebersold | |
| 5,538,897 A | 7/1996 | Yates et al. | |
| 5,856,082 A | 1/1999 | Aebersold et al. | |
| 6,064,754 A | 5/2000 | Parekh et al. | |
| 6,225,047 B1 | 5/2001 | Hutchens et al. | |
| 6,278,794 B1 | 8/2001 | Parekh et al. | |
| 6,316,267 B1 | 11/2001 | Bhalgat et al. | |
| 6,322,970 B1 | 11/2001 | Little et al. | |
| 6,329,209 B1 | 12/2001 | Wagner et al. | |
| 6,331,400 B1 | 12/2001 | Woods | |
| 6,872,575 B2 * | 3/2005 | Regnier | 436/174 |
| 7,052,915 B2 | 5/2006 | Aebersold et al. | |
| 7,052,916 B2 * | 5/2006 | Johnson | 436/86 |
| 7,122,377 B2 * | 10/2006 | Qiu et al. | 436/86 |
| 7,332,613 B2 * | 2/2008 | Gygi et al. | 548/303.7 |
| 7,422,865 B2 * | 9/2008 | Fischer | 435/23 |
| 2001/0039016 A1 | 11/2001 | Waldman et al. | |
| 2002/0106700 A1 | 8/2002 | Foote et al. | |

FOREIGN PATENT DOCUMENTS

| | | |
|---|---|---|
| WO | WO00/11208 A1 | 3/2000 |
| WO | WO01/96869 A1 | 12/2001 |
| WO | WO02/77016 A2 | 10/2002 |
| WO | WO02/97703 A2 | 12/2002 |
| WO | WO02/97703 A3 | 7/2003 |

OTHER PUBLICATIONS

Aebersold et al., "Equipping Scientists for the New Biology," Nat. Biotechnol., 2000, 18(4): 359.
Anderson et al., "Proteomics: Applications in Basic and Applied Biology," Curr. Opin. Biotechnol., 2000, 11(4): 408-412.
Appella et al., "Meeting report. Methods in Protein Structural Analysis Conference (MPSA2000), Charlottesville, Virginia, Sep. 16-20, 2000," Protein Sci., 2001, 10(2): 459-461.
Ashman et al., "Cell Signalling—The Proteomics of it All," Sci. STKE, 2001, 2001(103):pe33.
Beardsley et al., "Enhancing the intensities of lysine-terminated tryptic peptide ions in matrix-assisted laser desorption/ionization mass spectrometry," Rapid Commun. Mass Spectrom., 2000, 14(23): 2147-2153.
Cagney et al., "De Novo Peptide Sequencing And Quantitative Profiling Of Complex Protein Mixtures Using Mass-Coded Abundance Tagging," Nat. Biotechnol, 2002, 20(2): 163-170.
Chich, "A Mini Review: Proteomic Analysis, a Post-Genomic Approach," Le Lait, 2001, 81:13-18.
Dutt et al., "Proteomic Analysis," Curr. Opin. Biotechnol., 2000, 11(2): 176-179.
Eng et al., "An Approach to Correlate Tandem Mass Spectral Data of Peptides with Amino Acid Sequences in a Protein Database", J Am. Soc. Mass. Spectrom., 1994, 5: 976-989.
Ewing et al., "Peptide Fingerprinting on the OmniFLEX: Bench-Top Protein Identification," Bruker Daltonics, Inc., pp. 1-6.
Gevaert et al. "Chromatographic isolation of methionine-containing peptides for gel-free proteome analysis: identification of more than 800 *Escherichia coli* proteins," Mol. Cell. Proteomics, 2002,1(11): 896-903.

(Continued)

*Primary Examiner*—David M Naff

(57) ABSTRACT

The present invention provides a new and improved method for quantitative determination and/or identification of proteins in a sample. In one aspect, the invention provides a mass spectroscopic method for comparing protein levels in two or more samples by differentially isotopically labeling each sample's proteins' N- or C-termini. In another aspect, the invention provides a mass-spectroscopic method for identifying a sample as source for a protein from a mixture of two or more samples by differentially isotopically labeling each sample's proteins' N- or C-termini.

21 Claims, 1 Drawing Sheet

OTHER PUBLICATIONS

Gevaert et al., "Exploring Proteomes and Analyzing Protein Processing by Mass Spectrometric Identification Of Sorted N-Terminal Peptides," Nat. Biotechnol., 2003, 21(5): 566-569.

Gygi et al., "Measuring Gene Expression by Quantitative Proteome Analysis," Curr. Opin. Biotechnol., 2000, 11(4): 396-401.

Keough et al., "A method for high-sensitivity peptide sequencing using postsource decay matrix-assisted laser desorption ionization mass spectrometry," Proc. Natl. Acad. Sci. USA, 1999, 96(13):7131-7136.

Mann, "Quantitative Proteomics?" Nat. Biotechnol., 1999, 17(10): 954-955.

McCormack et al., "Direct analysis and identification of proteins in mixtures by LC/MS/MS and database searching at the low-femtomole level," Anal. Chem., 1997, 69(4): 767-776.

Pandey et al., "Proteornics to Study Genes and Genomes," Nature, 2000, 405(6788): 837-846.

Peters et al., "A Novel Multifunctional Labeling Reagent for Enhanced Protein Characterization with Mass Spectrometry," Rapid Commun. Mass Spectrom., 2001, 15(24):2387-2392.

Rapp et al., "Detection Limits of MALDI-TOF PSD for Peptide Sequencing from Protein Digests," Bruker Daltonics, 2000, pp. 1-6.

Shim et al., "PepAssem, A Peptide Assembly Algorithm for a Complex Protein Mixture," Genome Inform., 2001, 12: 366-367.

Suckau et al., "Automation of MALDI-TOF Analysis for Proteomics," Bruker Daltonics, 1999, pp. 1-5.

Suckau et al., "N-Terminal Derivatization of Tryptic Peptides for de Novo Sequencing by PSD: A Powerful New Tool in Proteomics," Bruker Daltonics, 2000, pp. 1-4.

Swiderek et al., "The identification of peptide modifications derived from gel-separated proteins using electrospray triple quadrupole and ion trap analyses," Electrophoresis, 1998, 19(6): 989-997.

Tang et al., "An Automated C-Terminal Sequencing Method for Analysis of Proteins Using an ABI 473A Sequencer," J Biomol. Tech., 1999, 10: 144-148.

Wilkins et al., "Rapid Protein Identification Using N-Terminal "Sequence Tag" and Amino Acid Analysis," Biochem. Biophys. Res. Commun., 1996, 221(3): 609-613.

* cited by examiner

MASS SPECTROSCOPIC METHOD FOR COMPARING PROTEIN LEVELS IN TWO OR MORE SAMPLES

This is a Continuation of application Ser. No. 10/341,310, filed on Jan. 13, 2003 now U.S. Pat. No. 7,422,865, the entire disclosure of which is incorporated herein by reference.

BACKGROUND OF THE INVENTION

Proteomics has emerged as a buzzword complement to genomics: it involves the qualitative and quantitative analysis of gene activity by assessment of protein, rather than RNA, level and/or activity. Proteomics includes the study of events such as post-translational modification of proteins, interactions between proteins, protein function and the location of proteins within the cell. Essentially, proteomics involves the study of part or all of the status of the total protein complement contained within or secreted by a cell, and thus offers a direct and promising look at the biological functions of a cell. In its simplest form, proteomics is an exercise in "mining" biological samples to identify which proteins are present in individual ones. The power of applied proteomics in drug discovery, however, lies in its ability to reveal key differences between the proteomes of, for example, normal and diseased cells. In principle, applied proteomics can reveal unique proteins or protein expression/activity patterns in diseased cells versus normal cells, and thereby can serve the task of molecular diagnosis of a particular disease or disorder. This goal could not be achieved, however, without massively parallel protein identification and characterization techniques.

Current technologies for the analysis of proteomes are based on a variety of protein separation techniques followed by identification of the separated proteins. The most popular method is based oil 2D-gel electrophoresis (2DE); see for example Parekh et al., U.S. Pat. Nos. 6,064,754 and 6,278,794. This technique allows the separation of proteins on an acrylamide gel according to their pI and molecular weight. Several hundred proteins can typically be visualized by radioactive or fluorescent labeling or silver staining. However, because the number of proteins in a sample can easily exceed 10,000 and because the number of resolved polypeptides shown in published 2DE databases typically ranges from about 1,000 to 3,000 per gel (See for example Julio Celis Database; http://biobase.dk/cgi-bin/celis), it soon became apparent that only the most abundant proteins in a crude protein mixture could be visualized by gel electrophoresis, highlighting the need for reducing proteomic sample complexity and improving proteomic detection methods.

The need for more sensitive, more accurate and higher-throughput technologies for performing analysis on proteomic material obtained from a variety of biological sources has lead to increasingly refined technologies for the identification of separated proteins. A significant breakthrough has been the mass spectrometric identification of gel-separated proteins: individual proteins (spots) may be excised from the gel for MS analysis. Identification strategies include peptide mapping, in which the masses of peptides produced by site-specific proteolysis are analyzed by mass spectrometry (MS) and correlated with unique mass patterns in protein databases. For example, a proteolytic enzyme such as trypsin (which cleaves polypeptides at arginine and lysine residues) can be used to fragment the extracted protein into two or more peptides. These peptides can then be analyzed by matrix assisted laser desorption ionization (MALDI)- or electrospray ionization (ESI)-mass spectrometry to determine their masses. The determined masses can then be used to screen a database to determine the amino acid sequences of the peptides.

In an alternative technique, direct analysis of highly complex peptide mixtures generated by the digestion of unseparated protein mixtures by liquid chromatography (LC)-MS/MS has provided an alternative to two-dimensional electroplhoresis, thereby obviating some of its limitations (e.g., poor detection capabilities of low abundance proteins and limited resolution in the gel separation). For example, peptide amino acid sequence data is obtained by tandem mass spectrometry (MS/MS), and used to screen databases for unique protein sequences (see for example, Eng et al., *J. Am. Soc. Mass Spectrom.* (1994) 5: 976; Yates III et al., *Anal. Chem.* (1995) 67: 3202; Yates III et al., *Anal. Chem.* (1995) 67: 1426; Figeys et al., *Anal. Chem.* (1996) 68: 1822). In this technique, selected peptide masses are isolated in the first stage of the spectrometer and subjected to collision-induced chemical dissociation, and the masses of the subfragments are then analyzed in the second stage to deduce the amino acid sequence. However this technique alone does not allow quantitative comparison between two similar proteomes (e.g., proteome of a normal cell versus a diseased cell, for example). Furthermore, a prominent problem inherent to proteomic analysis is that of sample complexity. As mentioned previously, the number of proteins in a given sample can easily exceed 10,000. After enzymatic digestion, the number of peptides present in a proteomic sample can reach the hundreds of thousands range. This level of complexity imposes an enormous burden on the analytical process and requires complex analytical techniques in combination with sophisticated computer-assisted technology to perform an otherwise time-consuming analysis.

Methods of simplifying the analysis of complex peptide mixtures by isolating signature peptides containing specific residues have been been proposed for proteomic analysis. These include the derivatization of cysteines in protein mixtures with thiol-specific biotin reagents and isolation of the biotinylated peptides from tryptic digests by binding to avidin (See Gygi et al., "Quantitative analysis of complex protein mixtures using isotope-coded affinity tags", *Nature Biotechnology*, 17(10): 994-999, 1999). Peptides containing histidine or glycosyl groups have also been isolated using immobilized metal affinity sorbents or lectin columns, respectively (Ji et al., "Strategy for qualitative and quantitative analysis in proteomics based on signature peptides", *J Chromatogr. B. Biomed. Sci. Appl.* 745(1): 197-210, 2000). These methods were used with isotopic labeling and MS analysis to identify and quantitate specific proteins in complex mixtures. Database searching in these cases is limited to those peptides containing the target amino acid or modification. Moreover, these approaches are not necessarily comprehensive as proteins that lack the target moiety are not represented in the isolated peptide mixture.

There remains a need for improved methods for efficiently and reliably identifying and quantifying proteins found in a proteomic sample, and preferably also reducing sample complexity.

SUMMARY OF THE INVENTION

Reduction of Sample Complexity

The present invention discloses a new and improved system for reducing the complexity of proteomic samples, while allowing identification of individual proteins in the samples. The system is based on a method for reducing the analysis of the original proteomic sample to that of a single peptide per protein in the original sample, each peptide being derived from the N-terminus (or C-terminus) of a protein present in the sample. For the purpose of this invention, where protein identification is based on the characterization of a peptide derived from the N-terminus of an individual protein, the method will be referred to as "N-terminal peptide selection method". Similarly, where protein identification is based on the characterization of a peptide derived from the C-terminus of an individual protein, the method is herein referred to as "C-terminal peptide selection method". More generally, the term "terminal peptide selection method" is used to refer to either method. When combined with well-known methods of mass spectrometry and computer-assisted database search systems, the inventive approach allows identification of proteins in a sample by characterizing a single N-terminally or C-terminally protected peptide generated for each protein. Methods known in the art can be applied to identify proteins in a sample from the amino acid sequences of N-terminal or C-terminal peptides generated by chemical or enzymatic means for each protein. Thus, the present invention provides an efficient method for reducing the complexity of a proteomic sample and identifying proteins in a complex mixture by reducing the analytical step to the characterization of a single peptide for each protein.

In one aspect, the invention encompasses methods for reducing the complexity of a proteomic sample. In certain embodiments, the inventive method comprises (i) providing one or more proteins; (ii) protecting the protein N- or C-termini with a suitable protecting agent; (iii) cleaving the terminally protected proteins with a suitable cleaving agent, thereby producing a mixture of terminally protected peptides and non-terminally protected peptides comprising free amino and carboxyl groups corresponding to the cleavage sites; and (iv) separating the terminally protected peptides from the peptide mixture, thereby reducing the sample complexity to one terminal peptide per sample protein.

In certain embodiments, separation of terminally protected peptides from the protein cleavage mixture is effected by (i) selectively immobilizing the non-terminally protected peptides on a solid support; (ii) washing the solid support with a suitable solvent; and (iii) collecting those solvent fractions containing the terminally protected peptides.

In one embodiment, non-N-terminally protected peptides are immobilized and the solid support comprises reactive groups which can form a covalent bond with reactive free amino groups. In another embodiment, noni-C-terminally protected peptides are immobilized and the solid support comprises reactive groups which can form a covalent bond with free carboxyl groups.

In another embodiment, the protecting group used to protect protein termini comprises a reactive group or a latent reactive group that can form a covalent bond with a solid support. Thus separation of the desired terminally protected peptides from the mixture is effected by immobilizing the terminally protected peptides on the solid support. The undesired peptides may be washed away from the solid support, and the terminally protected peptides may be released by exposing the solid support to a suitable releasing agent. Thus, in certain other embodiments, separation of terminally protected peptides from the protein cleavage mixture is effected by (i) selectively immobilizing the terminally protected peptides on a solid support; (ii) washing the solid support to remove peptides that are not covalently attached to the solid support; and (iii) releasing the terminally protected peptides from the solid support.

In another aspect, the invention encompasses methods for identifying proteins in a proteomic sample. In certain embodiments, the inventive method comprises (i) providing one or more proteins; (ii) protecting the protein terminal amino groups with a suitable protecting agent; (iii) cleaving the terminally protected proteins with a suitable cleaving agent, thereby producing a mixture of terminally protected peptides and peptides comprising free amino and carboxyl groups corresponding to the cleavage sites; (iv) separating the terminally protected peptides from the peptide mixture, thereby reducing the sample complexity to one terminal peptide per sample protein; and (v) detecting the terminally protected peptides.

In certain embodiments, steps (ii)-(iv) are carried out according to a method similar to that described for methods of reducing proteomic sample complexity described above.

In one embodiment, the methods described above are combined with a mass spectrometric technique for characterizing N-terminally or C-terminally protected peptides, and for identifying the proteins in the sample from which the N-terminally or C-terminally protected peptides were derived. In certain embodiments, the step of detecting utilizes a mass spectrometric technique. In one embodiment the mass spectrometric technique is tandem mass spectrometry and the terminally protected peptide MS fragmentation patterns are used to screen available databases to determine the amino acid sequence of the terminal peptides. In certain other embodiments, the amino acid sequence information is used to screen protein databases to identify the parent proteins from which the terminal peptides may be derived. In another embodiment, the mass spectrometric technique is coupled with a separation technique, such as High Pressure Liquid Chromatography (HPLC), gel electrophoresis or capillary electrophoresis (CE), and the mixture of N-terminally or C-terminally protected peptides is subjected to a separation step prior to MS analysis.

Quantitative Proteomics

In another aspect, the invention encompasses methods for quantitative comparison of protein levels that are differentially present between two samples, or protein(s) that is(are) present in some, but not all, samples. When combined with methods for differential isotopic labeling, the N-terminal or C-terminal peptide selection approach of this invention can be employed to quantify relative amounts of peptides and corresponding proteins in different samples.

In certain embodiments, the inventive quantitation method comprises (i) providing two or more samples each containing one or more proteins; (ii) protecting, in each sample, the protein N- or C-termini with a suitable protecting agent; (iii) cleaving, in each sample, the terminally protected proteins with a suitable cleaving agent, thereby producing for each sample a mixture of terminally protected peptides and peptides comprising free amino and carboxyl groups corresponding to the cleavage sites; (iv) separating, for each sample, the terminally protected peptides from the peptide mixture, thereby reducing the sample complexity for each of the two or more protein samples to one terminal peptide per sample protein; (v) differentially labeling the terminally protected peptides of each sample with a suitable reagent comprising a detectable label, thereby generating two or more sets of differentially labeled terminal peptides; and (v) measuring relative levels of differentially labeled terminally protected peptides.

In another embodiment, the method of quantitatively comparing protein levels in two or more'samples comprises steps of: (i) providing two or more samples each containing one or more proteins; (ii) differentially labeling each sample's protein N- or C-termini with a suitable protecting agent comprising a detectable label, thereby generating two or more sets of differentially labeled terminally protected proteins; (iii)

cleaving the differentially labeled terminally protected proteins with a suitable cleaving agent, thereby producing two or more mixtures of differentially labeled terminally protected peptides and peptides comprising free amino and carboxyl groups corresponding to the cleavage sites; (iv) separating, for each of the two or more peptide mixtures, the differentially labeled terminally protected peptides from the non-terminally protected peptides, thereby effectively reducing the sample complexity to one differentially labeled terminal peptide per differentially labeled sample protein; and (v) measuring the relative levels of differentially labeled terminally protected peptides.

In either one of the above two embodiments, combination of proteomic samples may be done any time after the step of differentially labeling terminal peptides or proteins in each sample, but before measuring the relative levels of labeled peptides in the mixture. This ensures that each differentially labeled peptic pair/set is analyzed simultaneously, thus allowing relative quantitation (as opposed to absolute quantitation which necessitates the creation of a calibration curve).

In certain exemplary embodiments, the method described directly above further comprises a step of combining the sets of differentially labeled terminally protected proteins prior to the step of cleaving and the method comprises steps of: (i) providing two or more samples each containing one or more proteins; (ii) differentially labeling each sample's protein N- or C-termini with a suitable protecting agent comprising a detectable label, thereby generating two or more sets of differentially labeled terminally protected proteins; (iii) combining the sets of differentially labeled terminally protected proteins; (iv) cleaving the differentially labeled terminally protected proteins with a suitable cleaving agent, thereby producing a combined mixture of differentially labeled terminally protected peptides and peptides comprising free amino and carboxyl groups corresponding to the cleavage sites; (v) separating the differentially labeled terminally protected peptides from the non-terminally protected peptides, thereby reducing the sample complexity to one differentially labeled terminal peptide per differentially labeled sample protein; and (vi) measuring the relative levels of differentially labeled terminally protected peptides.

In certain embodiments, the detectable labels used for differentially labeling each sample's protein N- or C-termini are differentially isotopically labeled. In certain exemplary embodiments, the detectable labels are differentially isotopically labeled using deuterium.

In certain embodiments, the step of differentially labeling the terminally protected peptides or proteins involves differentially labeling the N-terminally protected peptides, and the reagent comprising a detectable label is reacted with the C-terminal free carboxyl groups of the N-terminally protected peptides.

In certain embodiments, the step of differentially labeling the terminally protected peptides or proteins involves differentially labeling the C-terminally protected peptides, and the reagent comprising a detectable label is reacted with the N-terminal free amino groups of the C-terminally protected peptides.

In certain embodiments, the quantitative methods described above are combined with a mass spectrometric technique for characterizing the N-terminally or C-terminally protected peptides and for identifying the proteins in the sample from which the N-terminally or C-terminally protected peptides were derived. In certain embodiments, the step of detecting utilizes a mass spectrometric technique. In another embodiment the mass spectrometric technique is tandem mass spectrometry and the peptide MS fragmentation patterns are used to screen available databases to determine the amino acid sequence of the N- or C-terminal peptides. In certain other embodiments, the amino acid sequence information is used to screen protein databases to identify the parent proteins from which the terminal peptides may be derived. In another embodiment, the mass spectrometric technique is coupled with a separation technique, such as High Pressure Liquid Chromatography (HPLC), gel electrophoresis or capillary electrophoresis (CE), and the mixture of N-terminally or C-terminally protected peptides is subjected to a separation step prior to MS analysis.

In an exemplary embodiment, the detectable labels in different samples are differentially isotopically labeled, and quantitative comparison of levels of N-terminally or C-terminally protected peptides (hence, levels of corresponding proteins) in different samples is effected by comparing the relative amounts of the differentially isotopically labeled labels in the different samples.

The quantitative approach of the invention allows, for example, comparison of protein expression or modification in samples that are differentially affected by a change in condition or cell state (e.g., disease state, malignancy) of a cell, tissue or organism from which the sample originated, or by a stimulus (e.g., administration of a drug or contact with a potentially toxic material) or change in environment (e.g., nutrient level, temperature, passage of time), or in samples derived from different sources altogether (e.g., from different cell-types or different organisms or from transformed and/or genetically engineered cells such as cells obtained from site-directed mutation or gene knockouts experiments).

Kits of the Invention

Another aspect of the present invention relates to kits useful for conveniently performing a method in accordance with the invention. To enhance the versatility of the subject invention, the reagents and/or materials can be provided in packaged combination, in the same or separate containers, depending on the cross-reactivity and stability of the reagents and/or materials.

In one embodiment a kit, useful for identifying individual proteins in a proteomic sample, comprises: (i) one or more protecting agents for protecting protein N- or C-termini, and generating N- or C-terminally protected proteins; (ii) one or more cleaving agents for cleaving the terminally protected proteins into a mixture of terminally protected peptides and peptides comprising free amino and carboxyl groups; and (iii) means for separating the terminally protected peptides from the mixture.

In certain embodiments, the cleaving agents are chemical cleaving agents. In exemplary embodiments, the cleaving agents are enzymes for generating protein digests.

In certain embodiments, the kit of the invention further comprises a secondary protecting agent for selectively protecting the side chain lysine residues in the proteins.

In one embodiment, at least one protecting agent is an amine protecting agent for N-terminally protecting proteins in the sample. In another embodiment, at least one protecting agent is a carboxyl protecting agent for C-terminally protecting proteins in the sample. In yet another embodiment, the protecting agent comprises a reactive group or a latent reactive group that can form a covalent bond with a solid support.

In another embodiment, means for separating terminally protected peptides comprises a solid support. One or more solid supports may be provided with the kit, each being the same or different. In one embodiment, the solid support comprises reactive groups that can covalently bind to amines (for example for immobilizing non-N-terminally protected peptides). In another embodiment, the solid support comprises reactive groups that can covalently bind to carboxyl groups (for example for immobilizing non-C-terminally protected peptides). In yet another embodiment, the solid support is for immobilizing terminally protected peptides and the solid support comprises reactive groups that can covalently bind to the protecting group present on terminally protected peptides.

In certain embodiments, the kit comprises a reagent for releasing immobilized peptides from the solid support, if desired.

In another embodiment, the kit comprises a linker for immobilizing terminally protected or non-terminally protected peptides on the solid support.

In yet another embodiment, the kits of the invention are useful for quantitative comparison of protein levels that are differentially present between two or more samples, and further comprise one or more reagents for differentially labeling N-terminal or C-terminal peptides derived from proteins present in different samples. In one embodiment, the reagents are differentially isotopically labeled and are used to covalently modify the free carboxyl group of N-terminally protected peptides (or the free amino group of C-terminally protected peptides). In an exemplary embodiment, the protecting groups used to protect protein N-termini or C-termini in different samples comprise differentially isotopically labeled detectable labels. Thus quantitative comparison of levels of N-terminally or C-terminally protected peptides (hence, levels of the corresponding proteins) in different samples is effected by comparing the relative amounts of the differentially isotopically labeled labels in the different samples.

DEFINITIONS

"Proteomic sample": As used herein the term proteomic sample refers to a sample comprising a plurality of proteins. Preferably, the sample is the total protein complement of a cell, tissue or organism. In certain embodiments, the proteomic sample is a biological sample and refers to any solid or fluid sample obtained from, excreted by or secreted by any living organism, including single-celled micro-organisms (such as bacteria and yeasts) and multicellular organisms (such as plants and animals, for instance a vertebrate or a mammal, and in particular a healthy or apparently healthy human subject or a human patient affected by a condition or disease to be diagnosed or investigated). The biological sample can be in any form, including a solid material such as a tissue, cells, a cell pellet, a cell extract, cell homogenates, or cell fractions; or a biopsy, or a biological fluid. The biological fluid may be obtained from any site (e.g. blood, saliva (or a mouth wash containing buccal cells), tears, plasma, serum, urine, bile, cerebrospinal fluid, amniotic fluid, peritoneal fluid, and pleural fluid, or cells therefrom, aqueous or vitreous humor, or any bodily secretion), a transudate, an exudate (e.g. fluid obtained from an abscess or any other site of infection or inflammation), or fluid obtained from a joint (e.g. a normal joint or a joint affected by disease such as rheumatoid arthritis, osteoarthritis, gout or septic arthritis). The biological sample can be obtained from any organ or tissue (including a biopsy or autopsy specimen) or may comprise cells (whether primary cells or cultured cells) or medium conditioned by any cell, tissue or organ. Biological samples may also include sections of tissues such as frozen sections taken for histological purposes. Biological samples also include mixtures of biological molecules including proteins, lipids, carbohydrates and nucleic acids generated by partial or complete fractionation of cell or tissue homogenates. Although the sample is preferably taken from a human subject, biological samples may be from any animal, plant, bacteria, virus, yeast, etc. The term animal, as used herein, refers to humans as well as non-human animals, at any stage of development, including, for example, mammals, birds, reptiles, amphibians, fish, worms and single cells. Cell cultures and live tissue samples are considered to be pluralities of animals. In certain exemplary embodiments, the non-human animal is a mammal (e.g., a rodent, a mouse, a rat, a rabbit, a monkey, a dog, a cat, a sheep, cattle, a primate, or a pig). An animal may be a transgenic animal or a human clone. If desired, the biological sample may be subjected to preliminary processing, including preliminary separation techniques. For example, cells or tissues can be extracted and subjected to subcellular fractionation for separate analysis of biomolecules in distinct subcellular fractions, e.g. proteins found in different parts of the cell. See Deutscher (ed.), *Methods In Enzymology*, 182:147-238, 1990 (incorporated herein by reference in its entirety). Similarly, immunoprecipitation can be performed to identify antigenically related biomolecules such as proteins. See Firestone & Winguth In Deutscher, *Methods In Enzymology*, 182:688-699, 1990 (incorporated herein by reference in its entirety).

The biological sample can derive from a healthy subject or a subject suffering from a pathological condition. The biological sample can derive from cells of different genetic backgrounds, tissue origins, and/or stages of development, and can include, for example, bacteria, yeast, plant, insect and mammal cells. The proteomic sample may derive from normal, transformed (e.g., cells that were not derived from a cancer but were produced by laboratory treatment of normal cells), diseased or genetically engineered cells (e.g., from site-directed mutation or gene knockout experiments); or a cell previously exposed to an external stimulus (e.g., administration of a drug; contact with a potentially toxic material; change in nutrient level, temperature or passage of time).

"Protein": As used herein, the term protein refers to a peptide-linked chain of amino acids, regardless of post-translational modification, e.g., glycosylation or phosphorylation. Thus the term protein does not refer to a single entity, rather it encompasses proteins resulting from post-translational modifications and N- and/or C-terminal processing of the same gene product. Typically, a protein is an amino acid chain larger than 25 amino acid residues in length.

"Peptide": As used herein, the term peptide refers to an amino acid chain less than about 25 amino acid residues in length. For example, a plurality of peptides are produced by proteolytic fragmentation of a protein.

"Differentially present": As used herein, the term differentially present, as it relates to a protein in different proteomic samples, refers to a protein that is present in different samples but occurs with a change in a property inherent to the protein. As used herein the term property encompasses expression levels, protein modification (such as, for example, post-translational modifications), protein sequence (i.e., mutations) or protein function. For example, the term differentially present can be used when one or more proteins is present at a higher relative amount in a subset of the samples as compared to the remainder of the samples. The term also can be used when proteins are present in a subset of the samples that are not present in the remainder of the samples. Of course, it may be the case that proteins are present at a higher relative amount in a subset of the samples as compared to the remainder of the samples, while other proteins are present in a subset of the samples that are not present in the remainder of the samples.

"Affinity Label": As used herein, the term affinity label refers to a group, moiety, or entity that specifically interacts/associates with a counterpart entity (e.g., capture agent). The affinity label/capture agent pair is often referred to as an "affinity pair". The affinity pair may be a biochemical pair. Examples of biochemical pairs include antibody-antigen, enzyme-inhibitor, hormone-receptor, sugar-lectin and complementary nucleic acid components.

"Affinity Chromatography": As used herein, the term affinity chromatography refers to a separation method that utilizes the specific interaction between affinity pair components by chemically immobilizing one component of the pair on a solid support, packing it into a column, and then employing the column in conventional HPLC systems for the specific analysis of entities comprising the counterpart of the component pair. The affinity pair may be an antibody-antigen pair, and the solid support may comprise immobilized antibodies. One advantage of antibody-antigen affinity pairs is that any compound can be determined by this technique because specific antibodies can be raised to any chemical structure. The affinity pair may be an enzyme-inhibitor pair such as, for example, avidin/biotin. In this case, the substrate to be separated may be covalently attached to avidin and the resultant conjugate immobilized to a biotinylated solid support by affinity bonding between avidin and biotin. Alternatively, avidin may be attached to the solid support and the analyte to be isolated may be reacted to provide biotinyl terminations for immobilization on the solid support to which avidin has been attached.

"Associated with" or "Associate with": When two entities are associated with or associate with one another, as described herein, they are linked by a direct or indirect covalent or non-covalent interaction. Preferably, the association is covalent. Desirable non-covalent interactions include hydrogen bonding, van der Waals interactions, hydrophobic interactions, magnetic interactions, electrostatic interactions, affinity interactions or combinations thereof, etc.

"Cleaving agent": As used herein, the term cleaving agent refers to a reagent that will cleave a protein into two or more fragments under suitable conditions. Preferably the cleaving agent is an enzyme, most preferably one which cleaves the main chain of the polypeptide. Preferably the enzyme is trypsin, which cleaves proteins at the C-terminal end of many lysines and arginines. Other enzymes may be used to practice the invention, for example, chymotrypsin, pepsin, papain, proline endopeptidase, staph protease, elastase, protease K, AspN, lys-C, arg-C or glu-C. The cleaving agent is not limited to enzymes, but can be a chemical reagent, for example cyanogen bromide (CNBr), 2-nitro-5-thiocyanobenzoic acid, N-bromosuccinimide and other reactive halogen compounds, hydroxylamine, 1-2M formic or acetic acid, periodate oxidation, 2-(2-nitrophenylsulfenyl)-3-methyl-3-bromoindolenine or o-iodosobenzoic acid (See, for example, Hermodson et al., "Methods in Protein Sequence Analysis", ed. Elzinga, Humons Press, Clifton, N.J., pp. 313-323, 1982). The cleaving agent may be associated with a solid support to facilitate purification after protein cleavage and analysis of the resulting protein digests. For example, the enzyme can be physically trapped within the pores of porous beads of hydrophilic polymeric material. Alternatively, the enzyme may be immobilized onto the solid support via affinity bonding to a suitable capture agent present on the solid support. Thus, the enzyme could be covalently attached to avidin and the resultant conjugate attached to a biotinylated membrane by affinity bonding between avidin and biotin. Alternatively, avidin could be attached to the membrane and the enzyme could be reacted to provide biotinyl terminations for reaction with a membrane to which avidin has been attached.

"N-terminal peptide": As used herein, the term N-terminal peptide refers to peptides derived from protein N-termini in a proteomic sample, according to the N-terminal peptide selection method of the present invention. Alternatively, such peptides are referred to as N-terminally protected peptides.

"Non-N-terminal peptide": As used herein, the term non-N-terminal peptide refers to peptides, other than N-terminal peptides as defined herein, found in a mixture resulting from the chemical and/or enzymatic fragmentation of a protein sample, according to the N-terminal peptide selection method of the present invention. Alternatively, such peptides are referred to as non-N-terminally protected peptides.

"C-terminal peptide": As used herein, the term C-terminal peptide refers to peptides derived from the C-termini of proteins to be identified in a proteomic sample, according to the C-terminal peptide selection method of the present invention. Alternatively, such peptides are referred to as C-terminally protected peptides.

"Non-C-terminal peptide": As used herein, the term non-C-terminal peptide refers to peptides, other than C-terminal peptides as defined herein, found in a mixture resulting from the chemical and/or enzymatic fragmentation of a protein sample, according to the C-terminal peptide selection method of the present invention. Alternatively, such peptides are referred to as non-C-terminally protected peptides.

"Latent reactive group": The term latent reactive group, as used herein, refers to a group that must be activated for reaction. For example, it can be a group that carries a protecting group and which becomes reactive upon removal of the protecting group.

"Reactive free amino group": The term reactive free amino group, as used herein, refers to a group of the formula $-NR_1R_2$, wherein $R_1$ and $R_2$ are independently hydrogen or a substituted or unsubstituted, cyclic or acyclic, linear or branched, saturated or unsaturated aliphatic, alicyclic, heteroaliphatic or heteroalicyclic moiety. Preferably at least one of $R_1$ and $R_2$ is hydrogen. More preferably the aliphatic or alicyclic amine is a primary amine and both $R_1$ and $R_2$ are hydrogen. Most preferably, the nitrogen lone pair of electrons does not participate in electron delocalization (for example resonance, aromatic or tautomeric delocalization) and is minimally affected by other electronic effects (such as, for example, inductive/field effects) that would otherwise substantially decrease its nucleophile reactivity. In certain embodiments, the term reactive free amino group refers to the free N-terminal amino group of a protein and/or peptide.

"Substituted": In general, the term substituted refers to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Heteroatoms such as nitrogen may have hydrogen substituents and/or any permissible substituents of organic compounds described herein which satisfy the valencies of the heteroatoms. Examples of substituents include, but are not limited to aliphatic; alicyclic; heteroaliphatic; heteroalicyclic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; $-OH$; $-NO_2$; $-CN$; $-CF_3$; $-CH_2CF_3$; $-CHCl_2$; $-CH_2OH$; $-CH_2CH_2OH$; $-CH_2NH_2$; $-CH_2SO_2CH_3$; $-C(O)R_x$; $-CO_2(R_x)$; $-CON(R_x)_2$; $-OC(O)R_x$; $-OCO_2R_x$; $-OCON(R_x)_2$; $-N(R_x)_2$; $-S(O)_2R_x$; $-NR_x(CO)R_x$ wherein each occurrence of $R_x$ independently includes, but is not limited to, aliphatic, alicyclic, heteroaliphatic, heteroalicyclic, aryl, heteroaryl, alkylaryl, or alkylheteroaryl, wherein any of the aliphatic, alicyclic, heteroaliphatic, heteroalicyclic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted.

"Aliphatic": In general, the term aliphatic, as used herein, includes both saturated and unsaturated, straight chain (i.e., unbranched) or branched aliphatic hydrocarbons, which are optionally substituted with one or more functional groups, as previously defined. As will be appreciated by one of ordinary skill in the art, "aliphatic" is intended herein to include, but is not limited to, alkyl, alkenyl, alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (substituted, unsubstituted, branched or unbranched) having 1-6 carbon atoms. In certain embodiments, the alkyl, alkenyl and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms.

Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents, as previously defined. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

"Alicyclic": The term alicyclic, as used herein, refers to compounds which combine the properties of aliphatic and cyclic compounds and include but are not limited to cyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —CH$_2$-cyclopropyl, cyclobutyl, —CH$_2$-cyclobutyl, cyclopentyl, —CH$_2$-cyclopentyl-n, cyclohexyl, —CH$_2$-cyclohexyl, cyclohexenylethyl, cyclohexanylethyl, norborbyl moieties and the like, which again, may bear one or more substituents.

"Heteroaliphatic": The term "heteroaliphatic", as used herein, refers to aliphatic moieties in which one or more carbon atoms in the main chain have been substituted with an heteroatom. Thus, a heteroaliphatic group refers to an aliphatic chain which contains one or more oxygen sulfur, nitrogen, phosphorus or silicon atoms, e.g., in place of carbon atoms. Heteroaliphatic moieties may be saturated or unsaturated, branched or linear (i.e., unbranched), and substituted or unsubstituted. Substituents include, but are not limited to, any of the previously mentioned substitutents, i.e., the substituents recited above resulting in the formation of a stable compound.

"Heteroalicyclic": The term heteroalicyclic, as used herein, refers to compounds which combine the properties of heteroaliphatic and cyclic compounds and include but are not limited to saturated and unsaturated mono- or polycyclic heterocycles such as morpholino, pyrrolidinyl, furanyl, thiofuranyl, pyrrolyl etc., which are optionally substituted with one or more functional groups. Substituents include, but are not limited to, any of the previously mentioned substitutents, i.e., the substituenits recited above resulting in the formation of a stable compound.

"Carbodiimide": The term carbodiimide, as used herein, does not substantially differ from the common meaning of this term in the art, and refers to a moiety of structure $R_1$—N=C=N—$R_2$, wherein $R_1$ and $R_2$ are independently a substituted or unsubstituted, cyclic or acyclic, linear or branched, saturated or unsaturated aliphatic, alicyclic, heteroaliphatic, heteroalicyclic, aryl or heteroaryl moiety.

"Aryl": In general, the term aryl, as used herein, refers to stable mono- or polycyclic, unsaturated moieties having preferably 3-14 carbon atoms, each of which may be substituted or unsubstituted. Substituents include, but are not limited to, any of the previously mentioned substitutents, i.e., the substituents recited above resulting in the formation of a stable compound. The term aryl may refer to a mono- or bicyclic carbocyclic ring system having one or two aromatic rings including, but not limited to, phenyl, naphthyl, tetrahydronaphthyl, indanyl, indenyl and the like.

"Heteroaryl": The term heteroaryl, as used herein, refers to a stable heterocyclic or polyheterocyclic, unsaturated radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like. Heteroaryl moieties may additionally be substituted or unsubstituted.

It will also be appreciated that aryl and heteroaryl moieties, as defined herein may be attached via an aliphatic, alicyclic, heteroaliphatic, heteroalicyclic, alkyl or heteroalkyl moiety and thus also include -(aliphatic)aryl, -(heteroaliphatic)aryl, -(aliphatic)heteroaryl, -(heteroaliphatic)heteroaryl, -alkyl)aryl, -(heteroalkyl)aryl, -(heteroalkyl)aryl, and heteroalkyl)heteroaryl moieties. Thus, as used herein, the phrases "aryl or heteroaryl" and "aryl, heteroaryl, -aliphatic)aryl, -(heteroaliphatic)aryl, -(aliphatic)heteroaryl, -(heteroaliphatic)heteroaryl, -(alkyl)aryl, -(heteroalkyl)aryl, -(heteroalkyl)aryl, and -heteroalkyl)heteroaryl" are interchangeable.

"Carboxyl": The term carboxyl, as used herein refers to a group of formula —CO$_2$H.

"Amide": The term Amide, as used herein, does not substantially differ from the common meaning of this term in the art, and refers to a moiety of structure —C(O)NR$_1$R$_2$, wherein $R_1$ and $R_2$ are independently hydrogen or a substituted or unsubstituted, cyclic or acyclic, linear or branched, saturated or unsaturated aliphatic, alicyclic, heteroaliphatic, heteroalicyclic, aryl or heteroaryl moiety, or $R_1$ and $R_2$, taken together, form a substituted or unsubstituted heterocyclic or heteroaryl moiety.

"Carboxylic ester": The term carboxylic ester, as used herein, does not substantially differ from the common meaning of this term in the art, and refers to a moiety of structure —C(O)OR$_1$, wherein R$_1$ is a substituted or unsubstituted, cyclic or acyclic, linear or branched, saturated or unsaturated, aliphatic, alicyclic, heteroaliphatic, heteroalicyclic, aryl or heteroaryl moiety.

DETAILED DESCRIPTION OF CERTAIN EXEMPLARY EMBODIMENTS OF THE INVENTION

Figure 1:
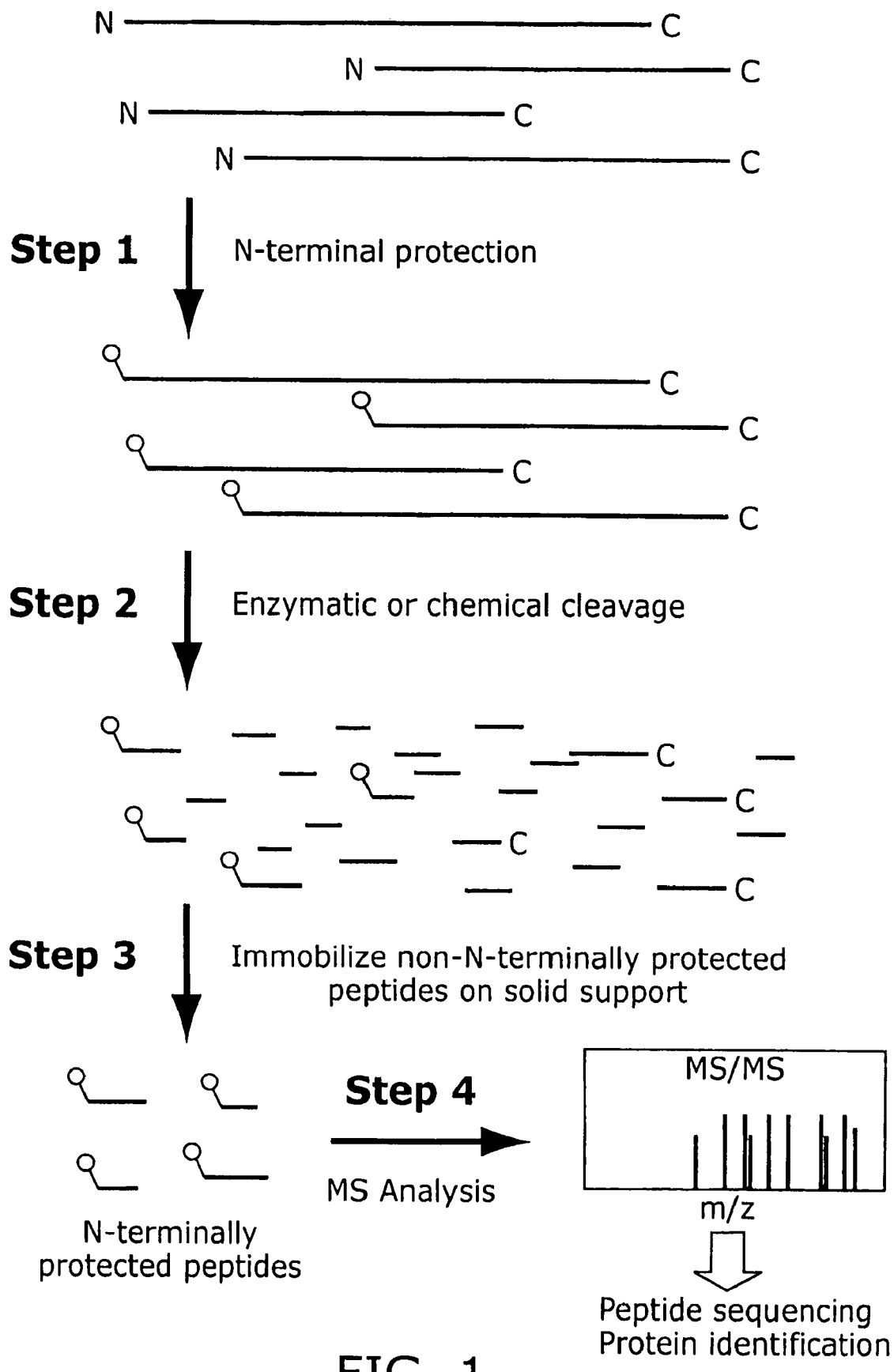
FIG. 1 illustrates one embodiment of the N-terminal peptide selection method of the invention.

Certain exemplary embodiments of the invention will now be more particularly described and pointed out in the following text. It will be understood that the particular embodiments of the invention are shown by way of illustration and not as limitations of the invention. Principle features of the invention may be employed in various embodiments without departing from the scope of the invention.

Strategies for target-driven drug discovery and rational drug design require identifying key cellular components, such as proteins, that are causally related to disease processes and the use of such components as targets for therapeutic intervention. However, present methods of analyzing biomolecules such as proteins are time consuming and expensive, and suffer from inefficiencies in detection, imaging, purification and analysis. It will be evident, therefore, that the present invention has huge potential for the automated identification and/or partial characterization of proteins, e.g., in proteomics research.

As discussed above, current technologies for identifying and characterizing proteins in complex samples typically rely on two-dimensional gel electrophoresis (2DE) coupled to mass spectrometry (MS). However, limitations inherent to 2DE (limited gel resolution capabilities for complex mixtures and difficulties in detecting (and thus quantitating) proteins of low abundance) have shifted the focus to MS as the technology base for quantitative proteomics. MS-based protcomics relies on the analysis of digested proteins into peptides by sequence-specific proteases, such as trypsin. Considering that the number of proteins in a given sample can easily exceed 10,000, enzymatic digestion can be expected to produce peptides numbering into the hundreds of thousands. This level of complexity imposes an enormous burden on the analytical process and requires complex analytical techniques in combination with sophisticated computer-assisted technology to perform the time-consuming analysis.

Addressing this difficult problem, the present invention provides a simple yet highly efficient method for identifying proteins in a proteomic sample by characterizing a single (selected) peptide per protein, thus dramatically reducing the sample complexity. In addition, the present invention provides a method for quantitating protein expression in different samples.

Reduction of Sample Complexity

A method that addresses the problem of protein sample complexity has recently been reported by Foote et al. (see U.S. Patent Application No. 2002/0106700). Briefly, Foote discloses a method for characterizing proteins in a given sample, which comprises isolating and analyzing C-terminal and/or N-terminal peptides from a mixture of peptides resulting from the enzymatic digestion of a protein mixture. Typically, the method involves enzymatically digesting a complex protein mixture into a mixture of peptides, separating the terminal peptides from the non-terminal peptides in the mixture, and characterizing the terminal peptides by conventional methods such as by 2D column separations coupled to MS. Information obtained from the characterization of the terminal peptides can be compared to databases including protein characterization data to correlate a given terminal peptide with a given protein.

In one variation of Foote's method, the step of separating terminal peptides from non-terminal peptides in the trypsin digest comprises contacting the mixture of terminal and non-terminal peptides with immobilized anhydrotrypsin, a catalytically inactive form of trypsin which binds to peptides having an arginine or lysine residue at the C-terminus. One limitation of this method is that not all proteins can be detected. Specifically, proteins having a C-terminal lysine or arginine are not represented, since their corresponding C-terminal peptide remains bound to the anhydrotrypsin support, together with the non-terminal peptides. Isolating and characterizing the C-terminal peptides of proteins having an arginine or lysine at the C-terminus requires an additional experiment in which an enzyme that does not cleave at these residues is used. Another limitation is that anhydrotrypsin separation implies the use of trypsin as the site-specific protease to generate the peptide mixture. Anhydrotrypsin column separation is not applicable to peptide mixtures resulting from fragmentation effected with other proteases (or chemical reagents) that do not cleave at the carboxyl side of arginine and/or lysine residues.

In another variation of Foote's method, non-terminal peptides may be separated from the desired terminal peptides by biotinylation of the non-terminal peptides followed by immobilization on an avidin or steptavidin affinity column. Alternatively, the N- or C-termini of proteins in the sample may be biotinylated and the N- or C-terminal peptides may be isolated on an avidin or steptavidin affinity column after fragmentation. However, proteins that are naturally blocked at the N- or C-terminal cannot be detected by this alternative method. In addition, the biotinylation reaction is unlikely to be completely selective for the N-terminal amine or C-terminal carboxyl, and biotinylation may occur on side-chain amino or carboxyl groups. Furthermore, because the biotin/avidin or streptavidin interaction is not 100% specific, total separation of terminal and non-terminal peptides by biotin/avidin affinity chromatography is not likely. Rather, contamination of terminal peptides with non-terminal peptides is likely to occur. In addition, biotin is a large functional group and may lead to interpretation problems in the analysis stage (e.g., MS).

The present invention addresses these limitations and discloses a new and improved system for reducing the complexity of a proteomic sample, while allowing identification of individual proteins in the sample. The inventive chemical approach has a broad scope of application and can be applied to mixtures of naturally-occurring proteins or peptides, as well as to mixtures of proteins or peptides derived from recombinant or synthetic methods.

The system reduces the analysis of the original proteomic sample to that of a single peptide per protein in the original sample, each peptide being derived from the N-terminus (or C-terminus) of proteins present in the sample. This 1:1 stoichiometry of peptide to parent protein allows straightforward characterization and/or quantitation of proteins in proteomic samples (e.g., quantitation of cellular gene expression levels). When combined with well-known methods of mass spectrometry and computer-assisted database search systems, the inventive terminal peptide selection approach allows identification of proteins in the sample by characterizing a single N- or C-terminal peptide generated for each protein. Methods known in the art can be applied to identify proteins in a sample from the sequences of N-terminal or C-terminal peptides generated by chemical or enzymatic means for each protein. Thus, the present invention provides an efficient system for identifying individual proteins in a complex mixture by reducing the analytical step to the characterization of a single peptide per protein.

N- or C-Terminal Peptide Selection Approach

In one aspect, the invention encompasses methods for reducing the complexity of a proteomic sample. In certain embodiments, the inventive method comprises (i) providing one or more proteins; (ii) protecting the protein N- or C-termini with a suitable protecting agent; (iii) cleaving the terminally protected proteins with a suitable cleaving agent, thereby producing a mixture of terminally protected peptides and non-terminally protected peptides comprising free amino and carboxyl groups corresponding to the cleavage sites; and (iv) separating the terminally protected peptides from the peptide mixture, thereby reducing the sample complexity to one terminal peptide per sample protein.

In certain embodiments, the protecting agent does not comprise an affinity label. In certain other embodiments, the step of separating the terminally protected peptides from the mixture does not involve affinity chromatography (e.g., biotin/avidin affinity chromatography).

In certain embodiments, in the step of protecting the protein N- or C-termini with a suitable protecting agent, the protecting agent comprises a radiolabel, a fluorescent label, a colorimetric label or an isotopic label.

In certain embodiments, in the step of protecting the protein N- or C-termini with a suitable protecting agent, side chain amino or carboxyl groups are simultaneously protected. In certain other embodiments, side chain amino or carboxyl groups are protected with a suitable secondary protecting agent. In certain exemplary embodiments, when utilizing the inventive N-terminal peptide selection approach, the protein lysine residues are preferably and selectively protected with a suitable secondary protecting agent prior to protein N-terminal protection, without affecting the ability of the proteins to be enzymatically cleaved by lysine-specific proteases (such as trypsin for example). Examples of such second protecting agent includes, but is not limited to, O-methyl-isourea or O-methyl imidazole and its chemical derivatives (e.g., substituted O-methyl imidazole). It is known in the art that these reagents selectively react with and protect lysine residues, without affecting free N-terminal amino groups, to generate trypsin cleavable lysine-protected proteins (See, for example, Beardsley et al., "Enhancing the intensities of lysine-terminated tryptic peptide ions in matrix-assisted laser desorption/ionization spectrometry", *Rapid Commun. Mass Spectrom.*, 14:2147-2153, 2000; and Peters et al., "A novel multifunctional labeling agent for enhanced protein characterization with mass spectrometry", *Rapid Commun. Mass Spectrom.*, 15:2387-2392, 2001).

In one embodiment, the method of this invention relies on the characterization of a single N-terminally protected peptide for each protein in the sample, and comprises the following steps: (i) providing one or more proteins; (ii) protecting the protein N-terminal amino groups with a suitable protecting agent; (iii) cleaving the N-terminally protected proteins with a suitable cleaving agent, thereby producing a mixture of N-terminally protected peptides and non-N-terminally protected peptides comprising free amino and carboxyl groups corresponding to the cleavage sites; and (iv) separating the N-terminally protected peptides from the peptide mixture, thereby reducing the sample complexity to one N-terminal peptide per sample protein.

In another embodiment, the inventive method relies on the characterization of a single C-terminally protected peptide for each protein in the sample, and comprises the following steps: (i) providing one or more proteins; (ii) protecting the protein C-terminal carboxyl groups with a suitable protecting agent; (iii) cleaving the C-terminally protected proteins with a suitable cleaving agent, thereby producing a mixture of C-terminally protected peptides and peptides comprising free amino and carboxyl groups corresponding to the cleavage sites; and (iv) separating the C-terminally protected peptides from the peptide mixture, thereby reducing the sample complexity to one C-terminal peptide per sample protein.

In exemplary embodiments, the protecting agent reacts selectively in good yield to give an N- or C-terminally protected protein that is stable to the projected reactions or experimental conditions. Preferably, but not necessarily, the protecting agent is selected so that it can be selectively removed in good yield by readily available, preferably non-toxic reagents that do not attack the other functional groups. Preferably, but not necessarily, the protecting agent has a minimum of additional functionality to avoid further sites of reaction.

In certain exemplary embodiments, the protecting agent is an amine protecting agent. Examples of suitable amine protecting agents include, but are not limited to, those that lead to the formation of carbamates (including methyl, ethyl, tert-butyl (e.g., Boc) and 9-fluorenylmethyl carbamates (e.g., Fmoc), to name a few), amides, cyclic imide derivatives, N-Alkyl and N-Aryl amines, imine derivatives, and enamine derivatives, to name a few. In certain exemplary embodiments, the protecting agent is acetic anhydride, di-tert-butyl dicarbonate (i.e., Boc anhydride) or 9-fluorenylmethoxy carbonyl reagent (i.e., Fmoc reagent) which generates a 9-fluorenylmethoxy carbamate upon reaction with a reactive free amine. Examples of Fmoc reagents suitable for practicing the invention include, but are not limited to, Fmoc-Cl, Fmoc-$N_3$, Fmoc-OBt (Bt=benzotriazol-1-yl), Fmoc-OSu (Su=succinimidyl) and Fmoc-$OC_6F_5$.

In certain embodiments, the protecting agent is a carboxyl protecting agent. Examples of suitable protecting agents include, but are not limited to, those that lead to the formation of carboxylic esters (for example, methanol or other lower aliphatic or alicyclic alcohol, diazomethane, MeI, $Me_3SiCHN_2$, $Me_2C(OMe)_2$, $CH_3OCH_2Cl$, $CH_3SCH_2Cl$, dihydropyraii, $CH_3OCH_2CH_2OCH_2Cl$, $PhCH_2OCH_2Cl$, $Me_3SiCl$, $Et_3SiCl$, $Me_2PhSiCl$), amides (for example, methyl amibe, ethyl amine, $Me_2NH$, pyrrolidine, piperidine) and hydrazide (for example, phenylhydrazine) derivatives, to name a few. The generation of carboxylic ester derivatives may involve (i) carboxylate activation with a good leaving group followed by displacement with a suitable nucleophile or (ii) nucleophile displacement of the carboxylate on an alkyl halide or sulfonate. In certain exemplary embodiments, the protecting agent is methyl iodide. In other embodiments, protection of the protein C-termini involves carbodiimide activation prior to reaction with a suitable protecting agent. For example, a protecting agent suitable for reaction with a carbodiimide-activated carboxyl group is an aliphatic amine. In certain embodiments, the aliphatic amine is methylamine or ethylamine.

It will be appreciated that the present invention is not intended to be limited to the protecting agents described herein; rather, a variety of additional equivalent protecting groups can be readily identified using the above criteria and utilized in the present invention, as referenced herein. Additionally, a variety of protecting groups are described in "Protecting groups in Organic Synthesis" Third Ed. Greene, T. W. and Wuts, P. G., Eds., John Wiley & Sons, New York: 1999, the entire contents of which are hereby incorporated by reference.

For the purpose of this invention, a cleaving agent is any reagent that converts a protein into two or more fragments under suitable conditions. Preferably the cleaving agent is one which cleaves the main chain of the polypeptide. Peptides generated by protein cleavage typically range in size from about 1 to about 50 amino acid residues in length and are more preferably sized to facilitate peptide sequencing using tandem mass spectrometric methods. More preferably the peptides range in size from about 5 to 50 amino acids. Most preferably, the peptides range in size from about 5 to 20 amino acids. Proteins may be readily cleaved into preferred lengths by many methods, including, for example, chemical methods or enzymatic methods, or a combination of the two. Representative chemical compounds that may be used to cleave proteins include cyanogen bromide (CNBr), 2-nitro-5-thiocyanobenzoic acid, N-bromosuccinamide and other reactive halogen compounds, hydroxylamine, 1-2M formic or acetic acid, periodate oxidation, 2-(2-nitrophenylsulfenyl)-3-methyl-3-bromoindolenine or o-iodosobenzoic acid. Representative enzymes include, for example, trypsin, chymotrypsin, pepsin, papain, proline endopeptidase, staph protease, elastase, protease K, AspN, Lys-C, Arg-C and Glu-C. In certain exemplary embodiments, the cleaving agent is an enzyme. Most preferably the enzyme is trypsin, which cleaves proteins at the C-terminal end of many lysines and arginines. Proteins can be digested using any appropriate methods known in the art. Those of ordinary skill in the art can select a protein digestion protocol suitable for use with the protein samples of interest.

1. Separation of Desired N- or C-terminal Peptides by Immobilization of Non-Terminal Peptides on a Solid Support In certain embodiments, the separation step of the inventive method comprises: (i) selectively immobilizing the non-terminally protected peptides on a solid support; (ii) washing the solid support with a suitable solvent; and (iii) collecting those solvent fractions containing the terminally protected peptides.

In exemplary embodiments, when the N-terminal peptide selection approach is used, separation of the N-terminally protected peptides from the mixture is effected by immobilizing the peptides containing a reactive free amino group (i.e., non-N-terminally protected peptides) on a solid support directly or indirectly through a linker, washing the solid support with a suitable solvent, and collecting the solvent fractions containing the desired N-terminally protected peptides.

In one embodiment the solid support comprises reactive groups which can form a covalent bond with free amino groups, and thus can immobilize non-N-terminally protected peptides present in the mixture. Thus, separation of the desired N-terminally protected peptides from the mixture is effected by immobilizing the non-N-terminally protected peptides on the solid support.

In certain other embodiments, when the C-terminal peptide selection approach is used, separation of the C-terminally protected peptides from the mixture is effected by immobilizing the peptides containing a free carboxyl group on a solid support directly or indirectly through a linker, washing the solid support with a suitable solvent, and collecting those solvent fractions containing the desired C-terminally protected peptides. In one embodiment the solid support comprises reactive groups which can form a covalent bond with the peptide free carboxyl groups.

In one embodiment the solid support comprises reactive groups which can form a covalent bond with free carboxyl groups and thus can immobilize non-C-terminally protected peptides present in the mixture. Preferably, but not necessarily, the non-C-terminal peptide free carboxyl group is activated with a carbodimide reagent prior to immobilization on the solid support. Thus, separation of the desired C-terminally protected peptides from the mixture is effected by immobilizing the non-C-terminally protected peptides on the solid support.

A variety of functionalized solid phase materials comprising reactive groups that can react with free amino groups or free carboxyl groups (for immobilization of undesired non-N-terminal or non-C-terminal peptides, respectively) are readily available from chemical suppliers. For example novaBiochem offers a wide variety of functionalized resins meeting these criteria. For instance, Br—, Cl—, carbonate-, CHO— or $CO_2H$— resins can be used for immobilizing non-N-terminal peptides. A exemplary solid phase material is a diisothiocyanate (DITC)-modified solid phase surface. Alternatively, $NH_2$—, OH— or SH— resins can be used for immobilizing non-C-terminal peptides. Other suitable solid phase materials will be readily apparent to one skilled in the art. A person of ordinary skill in the art will appreciate that the solid phase materials that can be used to practice the invention are not limited to those described herein. Rather, any solid phase material available in the art can be used to the extent that they are not inconsistent with the teachings of the invention.

In certain embodiments, where further analysis of the non-N-terminal peptides is desired, their release from the solid support may be effected under suitable conditions. For example, where a DITC-modified solid support is used, release of the non-N-terminal peptides from the solid support may be accomplished by exposing the solid support to a strong anhydrous acid, such as trifluoroacetic acid (TFA), Hydrochloric acid (HCl) or heptafluorobutanoic acid (HFBA).

2. Separation of the Desired N- or C-terminal Peptides by Immobilization on a Solid Support In certain embodiments, the separation step of the inventive method comprises: (i) selectively immobilizing the terminally protected peptides on a solid support; (ii) washing the solid support with a suitable solvent to remove peptides that are not covalently attached to the solid support; and (iii) releasing the terminally protected peptides from the solid support.

In another embodiment, the protecting group used to protect the protein N- or C-termini in the sample of interest comprises a reactive group or a latent reactive group that can form (or can be made to form) a covalent bond with a solid support directly or indirectly through a linker. Thus separation of the desired terminally protected peptides from the mixture is effected by immobilizing them on the solid support. The undesired peptides may be washed away from the solid support using a suitable solvent, and the terminally protected peptides may be released by exposing the solid support to a suitable releasing agent.

Preferably, the chemistry involved in immobilization of the terminally protected peptides through the N- or C-terminal protecting group does not invoke amine or carboxyl chemistry. Thus free amino groups and carboxyl groups should generally not be affected by the immobilization conditions and/or do not form covalent bonds with the solid support reactive groups.

Protein Identification

In another aspect, the invention encompasses methods for identifying proteins in a proteomic sample. In certain embodiments, the inventive method comprises (i) providing one or more proteins; (ii) protecting the protein terminal amino groups with a suitable protecting agent; (iii) cleaving the terminally protected proteins with a suitable cleaving agent, thereby producing a mixture of terminally protected peptides and peptides comprising free amino and carboxyl groups corresponding to the cleavage sites; (iv) separating the terminally protected peptides from the peptide mixture, thereby reducing the sample complexity to one terminal peptide per sample protein; and (v) detecting the terminally protected peptides.

In certain embodiments, steps (ii)-(iv) are carried out according to the N- or C-terminal peptide selection methods described above.

In one embodiment, the methods described above are combined with a mass spectrometric technique for characterizing N-terminally or C-terminally protected peptides, and for identifying the proteins in the sample from which the N-terminally or C-terminally protected peptides were derived. In certain embodiments, the step of detecting utilizes a mass spectrometric technique. In one embodiment the mass spectrometric technique is tandem mass spectrometry and the terminally protected peptide MS fragmentation patterns are used to screen available databases to determine the amino acid sequence of the terminal peptides. In certain other embodiments, the amino acid sequence information is used to screen protein database to identify the parent proteins from which the terminal peptides may be derived. In another embodiment, the mass spectrometric technique is coupled with a separation technique, such as High Pressure Liquid Chromatography (HPLC), gel electrophoresis or capillary electrophoresis (CE), and the mixture of N-terminally or C-terminally protected peptides is subjected to a separation step prior to MS analysis.

General Considerations Regarding Peptide Immobilization Methods

In certain embodiments, peptides (either terminal or non-terminal, depending on which peptide separation approach is used) may be separated from the chemical and/or enzymatic protein cleavage mixture by covalent binding to a solid support either directly (as described above) or indirectly through a linker. For example, a solid support may be chemically modified prior to immobilization of the intended peptides by reacting it with a linker comprising two reactive groups. One of the reactive groups will be such that it can form a covalent bond with the reactive groups present on the solid support. The second reactive group on the linker moiety will be such that it can form a covalent bond with a pre-determined functionality present on the peptides to be immobilized. Alternatively, the peptides may be reacted with the linker prior to immobilization on the solid support, and the peptide-linker conjugate may then be immobilized on the solid support by reaction of the remaining reactive group on the linker with the reactive groups present on the solid support surface.

Preferably the linker moiety is substantially chemically inert (e.g., minimally interferes with subsequent chemical reactions). In addition, when it is present in the terminal peptide to be analyzed or in the peptide solution to be analyzed, the linker moiety preferably does not significantly interfere with mass spectral analysis and sequencing of the peptides by tandem mass spectrometric methods. For example, the linker moiety is preferably minimally ionized during mass spectrometric analysis and preferably does not undergo peptide-like fragmentation. When it is present in the terminal peptide to be analyzed, it preferably does not significantly suppress ionization of the peptides. Most preferably, the linker comprises functional groups or moieties that facilitates ionization of the peptides containing it. Examples of functionalities suitable for enhancing ionization include acidic groups (e.g., COOH), basic groups (e.g., amino groups) or charged groups (e.g., ammonium or phosphonium groups). In exemplary embodiments, the linker moiety is chemically, photochemically or enzymatically cleavable. Photolabile linkers are well-known in the art and include, for example, those comprising an o-nitrobenzyl moiety (see, for example, www.innovachem.com/Reference.htm). See also Garigipati et al., "Photolytically cleavable encoding and linking agents for use in combinatorial chemistry", U.S. Pat. No. 6,075,166. Cleavable linkers also include moieties having disulfide bonds and acid or base labile groups (for example, silyl ethers, carbamates and thioesters, to name a few). For examples of enzymatically cleavable linkers, see Lebl et al., "Topologically segregated, encoded solid phase libraries comprising linkers having an enzymatically susceptible bond", U.S. Pat. No. 6,090,912.

In certain embodiments, where separation of the desired N- or C-terminal peptides is effected by immobilization (of terminal or non-terminal peptides) on a solid support, washing of the unbound peptides from the solid support surface may be desired. Preferably, the wash solvent is selected so that it is compatible with the linkage immobilizing the peptides to the solid support, and does not cause the release of the bound peptides from the solid support. Preferably, the linkage between bound peptides and the solid phase surface should withstand extensive and multiple washes with a variety of solvents with little or no "bleeding" of the bound peptides from the solid support (e.g., the linkage peptide-solid support is substantially stable to multiple solvent washings). A person of ordinary skill in the art will know how to select a suitable solvent depending on the chemical nature of the linkage between the non-terminal peptides and the solid support.

In certain embodiments, release of bound peptides from the solid support may be desired and peptide release is effected with a suitable releasing agent. Selection of the releasing agent will depend on the chemical nature of the linkage between the peptides and the solid support. Preferably, but not necessarily, the releasing agent and/or the conditions used to effect release of the peptides from the solid support are selected so that any modifications to the peptides that are retained on release from the solid support do not significantly interfere with mass spectral analysis and sequencing of the peptide by tandem mass spectrometric methods. In certain embodiments, the releasing agent and/or the conditions used to effect release of the peptides from the solid support are selected so that any modifications to the peptides that are retained on release from the solid support facilitate ionization of the peptides. Examples of suitable modifications are described herein and will readily be apparent to the person skilled in the art.

For example, where the peptides are terminal peptides covalently bound to the solid support, the releasing agent will be preferably, but not necessarily, selected so that it effects the release of the terminal peptides from the solid support whereby the N- or C-terminal protecting group is retained on the peptides. Alternatively, the releasing agent simultaneously releases the terminal peptides from the solid support and effects the removal of the protecting group at the terminus of the desired peptides. Similarly, where the terminal peptides are covalently immobilized on the solid support indirectly through a linker, the releasing agent may be selected so that it effects the release of the terminal peptides from the solid support where both the terminal protecting group and the linker are retained on the peptides. Alternatively, the releasing agent may be selected so that it effects the release of the terminal peptides from the solid support where only the terminal protecting group is retained on the peptides (the linker moiety is cleaved from the peptides). Alternatively, the releasing agent may be selected so that it simultaneously releases the terminal peptides from the solid support and effects the removal the protecting group at the terminus (hence the linker as well) of the desired peptides. A person of ordinary skill in the art will known how to select the releasing agent to effect the desired cleaving reaction.

Preferably, chemical transformations of peptides performed for the specific purpose of separating terminally protected peptides from non-terminally protected peptides are compatible with the chemistry involved in the separation process. For example, where separation of N-terminally protected peptides via immobilization of the corresponding non-N-terminally protected peptides is intended, chemical transformations at the free amino group of the non-N-terminal peptides for immobilization on a solid support, either directly or indirectly through a linker, will be compatible with and will not alter the N-terminal protecting group on the desired N-terminal peptides. Preferably, but not necessarily, the chemical transformations performed at the reactive free amino group of the non-N-terminal peptides for immobilization on a solid support, either directly or indirectly through a linker, will be compatible with and will not alter the free carboxyl group at the C-terminal of the desired N-terminal peptides. Alternatively, the free C-terminal carboxyl moiety of the peptides in the mixture may be protected with a suitable protecting agent prior to any transformation of the undesired peptides' free amino group, or subsequent to transformations of the undesired peptides' reactive free amino group but prior to immobilization of the undesired non-N-terminal peptides on the solid support. A variety of amino and carboxyl protecting groups are known in the art, as referenced herein, and will be readily apparent to the reader who wishes to practice the invention. Preferably, chemical transformations incurred by the desired N- or C-terminal peptides prior, during or after separation from the sample mixture do not significantly interfere with mass spectral analysis and sequencing of the peptide by tandem mass spectrometric methods.

One of ordinary skill in the art will appreciate that the methods used to separate the N-terminal or (C-terminal) peptides from the peptide mixture resulting from the chemical or enzymatic fragmentation of the proteomic sample of interest are not limited to those recited herein. Rather, any available techniques suitable to effect separation the desired terminal peptides from the fragmentation mixture can be used.

Mass Spectrometric Methods

In one embodiment, the N- or C-peptide selection method described above is combined with a mass spectrometric technique for characterizing the N-terminally or C-terminally protected peptides and for identifying the proteins in the sample from which the N-terminally or C-terminally protected peptides were derived. The isolated peptides are characteristic of the presence of a protein in the original sample. In particular, the sequence of isolated peptides can be determined using tandem MS techniques, and by application of sequence database searching techniques known in the art, the protein from which the sequenced peptide originated can be identified.

In an effort to more fully describe the state of the art to which the invention pertains, provided below are references relating to the application of mass spectrometric techniques to protein identification and proteome analysis: Akhilesh P. et al., "Proteomics to study genes and genomes", *Nature,* 405: 837-846, 2000; Dutt M. J. et al., "Proteomic analysis", *Curr Opin Biotechnol.,* 11:176-179, 2000; Gygi S P, et al., "Mass spectrometry and proteomics", *Curr Opin Chem Biol.,* 4 (5): 489-94, 2000; Gygi S P, et al., Goodlett D R, et al, "Protein identification with a single accurate mass of a cysteine-containing peptide and constrained database searching.", *Anal Chem.,* 72 (6): 1112-8, 2000; Anderson N. L et al., "Proteomics" applications in basic and applied biology", *Curr Opin Biotechnol.,* 11:408-412, 2000; and Little et al., U.S. Pat. No. 6,322,970. Each of these references is incorporated by reference herein to the extent that they are not inconsistent with the disclosure of this application.

Suitable mass spectrometry techniques include, but are not limited to, matrix-assisted laser desorption/ionization combined with time-of-flight mass analysis (MALDI-TOF MS) or electrospray ionization mass spectrometry (ESI MS). See, for example, Patterson & Aebersold, *Electrophoresis,* 16: 1791-1814, 1995; and Figeys et al., *Anal. Chem.,* 68: 1822-1828, 1996. Matrix-assisted laser desorption ionization (MALDI) used in conjunction with a time-of-flight (TOF) mass analyzer holds great potential for identifying peptides because of its relatively broad mass range, high resolution (10,000 at mass 5,000) and sampling rate (up to 1 sample/second). In one aspect MALDI offers a potential advantage over ESI and FAB in that biomolecules of large mass can be ionized and analyzed readily. Furthermore, in contrast to ESI, MALDI produces predominantly singly charged species. In one embodiment, the N-terminal or C-terminal peptides generated from the protein sample are analyzed by MALDI-TOF MS according to methods known in the art. Typically, this involves forming a matrix on the membrane with an agent which absorbs the incident light strongly at the particular wavelength employed. The sample is excited by UV, or IR laser light into the vapor phase in the MALDI mass spectrometer. Ions are generated by the vaporization and form an ion plume. The ions are accelerated in an electric field and separated according to their time of travel along a given distance, giving a mass/charge (m/z) reading which is very sensitive.

The protecting agents used in accordance with the teachings of the invention are preferably selected so as to not significantly interfere with mass spectral analysis and sequencing of the peptide by tandem mass spectrometric methods. Preferably, but not necessarily, the protecting agents are selected so as to impart desirable characteristics to the analysis. Examples of such characteristics include decreasing the laser energy required to volatilize the peptide, facilitating ionization, creating predominantly singly charged ions, reducing the peak width, and increasing the sensitivity and/or selectivity of the desired analysis product. When the desired N-terminal or C-terminal of the invention are isolated by immobilization on a solid support via covalent bonding of the protecting group to the solid support, either directly or indirectly through a linker, the protecting agents used in this method are preferably selected so that any modifications to the peptide that are retained on release from the solid support do not significantly interfere with mass spectral analysis and sequencing of the peptide by tandem mass spectrometric methods.

An interesting feature of MS analysis of peptides is the ability to generate different types of structural information about a particular peptide of interest. For example, the mass spectrometer can readily provide information on the mass of a particular peptide and can also be used to generate de novo amino acid sequence information from tandem mass spectra obtained either by postsource decay or collision-induced dissociation. See, for example, End el al., "An Approach to Correlate Tandem Mass Spectral Data of Peptides with Amino Acid Sequences in a Protein Database", *J. Am. Soc. Mass Spectrom.*, 5:976-989, 1994; Swiderek K. et al. "The identification of peptide modifications derived from gel-separated proteins using electrospray triple quadrupole and ion trap analyses", *Electrophoresis*, 19:989-997, 1998; and Keough T. et al. "A method for high-sensitivity peptide sequencing using postsource decay matrix-assisted laser desorption ionization mass spectrometry", *Proc. Natl. Acad. Sci USA*, 96:7131-7136, 1999. For example, peptide sequencing may be performed with a computer assisted sequencing technique in which the molecular mass of the peptide is accurately determined by MS. A computer is used to determine all possible combinations of amino acids that can sum to the measured mass of the peptide (parameters related to water lost in forming peptide bonds, protonation, other factors that alter the measured mass of amino acids or otherwise constrain the allowed combinations of amino acids may be taken into consideration). A library of all allowed linear permutations of amino acids is then generated. The algorithm can then calculate theoretical fragmentation spectra for each member of the allowed library of permutations and compare them with an experimental fragmentation spectrum of the unknown peptide obtainable by mass spectrometry. The theoretical fragmentation spectrum most closely matching the experimental fragmentation pattern reveals the amino acid sequence of the unknown peptide.

In one embodiment the mass spectrometric technique is tandem mass spectrometry and the amino acid sequence of the N-terminally or C-terminally protected peptides is determined. Typically, any given peptide entering the tandem mass spectrometer is selected and subjected to collision induced dissociation (CID). The spectra of a resulting fragment ion is recorded in the second stage of the mass spectrometry, as a so-called CID spectrum. This process is repeated with other (ideally all) peptides present in the sample. Because the CID process usually causes fragmentation at peptide bonds and different amino acids for the most part yield peaks of different masses, a CDI spectrum alone often provides enough information to determine a peptide sequence. Alternatively, the peptides may be separated and purified and their sequences determined with an automated sequencer. Many methods well known to those skilled in the art may be utilized to purify the peptides prior to determining its amino acid sequence. Representative examples include high pressure liquid chromatography (HPLC), reverse-phase high pressure liquid chromatography (RP-HPLC), gel electrophoresis, capillary electrophoresis (CE), or other suitable chromatographic techniques. In addition, automated sequenators are known in the art (for example, Applied Biosystems ABI 470). Typically, the automated sequencer performs an Edman degradation in which the amino acids are derivatized and removed sequentially from the N-terminus of the peptide or protein. The amino acid derivatives are then identified after HPLC separation allowing the amino acid sequence of the protein/peptide to be deduced. In this case, the N-terminally protected peptides of the invention may be deprotected prior to automated sequencing, since Edman degradation does not proceed when the N-terminal residue of the peptide is blocked. In exemplary embodiments, tandem mass spectrometry is used to determine the amino acid sequence of the peptides.

In another embodiment, the mass spectrometric technique is directly or indirectly coupled with a liquid chromatography technique, such as HPLC, RP-HPLC CE or gel electrophoresis to further resolve the N-terminally or C-terminally protected peptides prior to MS analysis. This is particularly useful for resolving peptides of identical or similar molecular weight. HPLC and CE are exemplary chromatographic methods for practicing the invention. CE has an extremely high resolving power (separations with several million theoretical plates have been documented), the solvent flow in CE separations is very slow and is induced by the electroosmotic effect. Thus the flow is dependent on the pH of the solvent. In addition, it does not suffer from any "wall" or diffusion effects which could adversely affect the separation. See Aebersold R. H, U.S. Pat. No. 5,240,859; Clauser et al., *Proc. Natl. Acad. Sci. USA*, 92: 5072-5076, 1995; Ducret et al., *Electrophoresis*, 17: 866-876, 1996; Gevaert et al., *Electrophoresis*, 17: 918-924, 1996.

Once the amino acid sequence of the isolated N-terminal or C-terminal peptides has been experimentally determined, a computer program can be used to search available databases for matching amino acid sequences and identify the original proteins from which the peptides were derived. Various informatics tools are known in the art that can perform this task. For example, a valuable resource for internet-accessible proteome databases is the Expert Protein Analysis System (ExPASy), available online at http://vww.expasy.ch/. Several databases in FASTA (ASCII text) format with protein sequence information can be accessed with standard web-browsing software over the world wide web (WWW). These include, for example, the SWISS-PROT database (http://www.expasy.ch/sprot/) and OWL database (http;/www.biochem.ucl.ac.uk/bsm/dbbrowser/OWL/OWL.htmnl). Other protein databases include Incyte Genomics' Yeast Protein Database (YPD), WonnPD, HumanPSD and G-Protein Coupled Receptor Protein Database (GPCR-PD), to cite a few (See: http://www.incyte.com/sequence/proteome/index.shtml).

The sequence database may be a protein or a nucleic acid sequence database. As will be recognized by those skilled in the art, a nucleic acid sequence database may be searched by using the standard genetic code to determine the possible nucleic acid sequences which encode the signature peptides. Examples of nucleotide databases include, for example, express sequence tag (EST) databases and raw genomic sequence databases. For example the amino acid sequence can be reverse translated to generate a cDNA probe. The probes can then be used to screen a cDNA library and resulting cDNA clones can be used to screen a genomic library. The gene encoding the protein can then be identified by sequence analysis. The identity of the gene can be confirmed by determining the intron-exon structure of the gene, cloning the exons into a vector and performing in vitro transcription/translation to express the protein or by expressing the protein in vivo. The expressed protein can then be analyzed according to the method of the invention and the results compared with that obtained for the unknown protein. The gene is confirmed as encoding the original protein if the analysis results between the expressed protein and the original protein are substantially the same. Procedures for all of these manipulations are well established and known to those of skill in the art and/or are described herein. One of ordinary skill in the art will appreciate that consideration may be given to the species from which the protein was obtained, and the cDNA probe may be designed to include only codons preferred in the relevant species (e.g. codons preferred in humans, where the protein is a human protein). Nucleotide sequence databases contain sequences for expressed sequence tags (ESTs), which correspond to expressed genes and gene fragments. EST sequence databases, such as the ESTdb at the National Center for Biotechnology Information (http:/www.ncbi.nlm.nih.gov/dbEST/index.html) can be accessed in the same manner as protein sequence databases. Database searching can be carried out with computer-assisted database search programs, such as SEQUEST (Trademark, University of Washington, Seattle Wash.). See, for example, McCormack, A. L. et al. "Direct Analysis and Identification of Proteins in Mixtures by LC/MS/MS and Database Searching at the Low-Femtomole Level", *Anal. Chem.,* 69:767-776, 1996; Eng, J. K. et al. "An Approach to Correlate Tandem Mass Spectral Data of Peptides with Amino Acid Sequences in a Protein Database" *J. Amer. Soc. Mass. Spectrom.,* 5:976-989, 1994; Yates, III et al., U. S. Pat. No. 5,538,897; and Aebersold et al., WO 01/96869. For example, such program can operate to take all known genomic sequences, compute all possible theoretical CID spectra and compare them to experimental CID spectra for matches and sequence identification. In addition, certain known information (e.g., mass modification to the C-terminus, glutamic acid, aspartic acids and any other acidic side groups, and mass changes due to phosphorylation or other post-translational modifications) may be taken into consideration in the computer analysis.

As one of ordinary skill in the art will appreciate, advantages of the present method are numerous, including simplicity and time- and cost-efficiency. A significant feature is the dramatic reduction in sample complexity, compared to methods currently utilized in the field: the analytical step is reduced to the characterization of a single peptide per protein in the original sample. In addition, the location of the target peptide on the original protein is inherently known: it is either N-terminal or C-terminal, depending on whether the N-terminal or C-terminal peptide selection method is used. Knowledge of both the peptide amino acid sequence and its location in the protein from which it is derived allows identification of the protein with a very high degree of certainty, provided that the protein is known and information relevant to its structure is available in computer-searchable databases. Furthermore, the method can use inexpensive reagents and well-known chemistry. The method is also compatible with disulfide bond reduction and alkylation of cysteine. In addition, mixture complexity due to post-translational modifications (other than in the terminal peptide) is reduced, making the analysis and characterization process less difficult. Furthermore, naturally N- or C-blocked proteins can be detected.

In certain embodiments, additional information can be generated, such as, for example, knowledge about which proteins are N-terminally (or C-terminally) blocked in the original proteomic sample. The use of a well chosen protecting agent in the initial N-terminal (or C-terminal) protection step allows this determination: N-terminal (or C-terminal) peptides not carrying the specific protecting group must have been blocked initially. This may be accomplished by selecting an N-terminal (or C-terminal) protecting agent that bears a detectable (and distinctive) label, such as, for example, a radioactive label, a colorimetric label, an isotopically labeled label or a fluorescent label.

In other embodiments, the sequence of the first 10-20 residues at the N-terminal of a protein generally gives sufficient information to allow (i) assigning the site of proteolytic maturation, (ii) synthesizing oligonucleotide probes for specific cDNA isolation, and (iii) identifying the protein in databases (as discussed above) and (iv) subsequently aligning the protein against DNA sequences. The advent of mass spectrometry also allows access to such information as glycosylation patterns, phosphorylation and other post-translational modifications on the protein termini.

In yet other embodiments, the present invention can provide sequence information of the C-terminus of proteins, and therefore proves useful for confirming the integrity of the C-terminus of proteins. This has important quality control implications in the establishment of the fidelity of protein expression, particularly with respect to recombinant proteins of biotechinological importance (e.g., products for the food, agricultural and medical industries). C-terminal processing is recognized as an important post-translational modification, sometimes critically affecting the structure and activity of a protein. Thus, the inventive method may help provide insight into C-terminal protein structure and processing mechanisms, as well as diseases and/or disease states that have been associated with impaired protein processing.

In still other embodiments, the method of the invention is compatible with quantitation which in turn allows access to global studies of protein expression.

Quantitative Proteomics

A significant body of work in the field of proteomics involves the characterization of biological sample proteomes: for example, tracking the changes in a proteome over time (dynamic analysis), or identifying differences in protein expression or modification between samples or sample treatments. The presence or relative abundance of a particular protein found in one sample and not another can be the basis for diagnostic tests or lead to the identification of targets for drug development. General studies of protein expression in samples of different genetic backgrounds, disease states, etc allow the evaluation of multiple factors susceptible to contribute in the manifestation of diseases. For example, the identification of proteins (and pathways) affected by a particular disease can be used to identify better drug targets. In addition, a proteomic approach to drug discovery offers the possibility of evaluating the suitability of a drug therapy to a particular phenotype. This highlights the importance of proteomics in drug discovery and underlines the value of analytical methods capable of cheaply, reliably and efficiently quantilating proteins in proteomic samples.

As discussed herein, quantitative proteomics has traditionally relied on two-dimensional gel electrophoresis to identify proteins that are up- or down-regulated in a disease-specific manner, the ultimate goal being to use those proteins that are differentially present as diagnostic markers or therapeutic targets. However, technical challenges associated with this method significantly limit the scope of its applications. Such limitations stem from the fact that (i) hydrophobic and large proteins usually do not enter the second dimension of the gel, and (ii) dynamic ranges makes it difficult to visualize all but the most abundant proteins, particularly in body fluids such as serum or cerebrospinal fluid where more than 99% of the protein complement consists of serum albumin and globulins.

An alternative approach to quantitative proteomics is the so-called protein chip approach where a variety of "bait" proteins such as antibodies are immobilized in an array format onto specially treated surfaces (see Wagner el al., U.S. Pat. No. 6,329,209 and Lueking A. el al., "Protein microarrays for gene expression and antibody screening", *Anal. Biochem.,* 270:103-111, 1999). Typically, the surface is exposed to the sample of interest and the proteins that specifically bind to the relevant antibodies are immobilized on the chip surface. For example the protein chip is exposed to fluorescently labeled proteins from two different cell states: the cell lysates are labeled by different fluorophores and mixed so that the color acts as a readout for the change in abundance of the protein bound to the antibody on the chip. This technique, however, depends on the availability of specific and well-characterized antibodies for protein identification and quantitation, and is not general to all proteins in a given sample.

Recently, MS-based quantitative proteomic analysis was rendered possible with techniques such as those based on isotope-coded affinity tags (ICAT). See Aebersold et al., international patent application Nos: WO 01/96869 and WO 00/11208; Gygi S. P. et al. "Quantitative analysis of protein mixtures using isotope coded affinity tags", *Nat. Biotechnol.*, 17: 994-999, 1999. ICAT involves site-specific, covalent labeling of protein with isotopically normal or heavy ICAT reagents, which, as shown below, typically consist of (1) a thiol reactive group that is selective for cysteines, (2) an ethylene glycol linker that occurs in deuterated and isotopically normal forms and provides the basis for quantification, and (3) biotin which provides an affinity tag for the selective isolation of tagged peptides.

sample complexity (i.e., analysis reduced to that of a single peptide per protein in the original proteomic sample).

In one aspect this invention provides a system for determining whether a protein is differentially present (e.g., differentially expressed or modified) in a first and second biological sample: when combined with methods for differential labeling of the peptides, the N-terminal or C-terminal peptide selection method of this invention can be employed to quantify relative amounts of peptides and corresponding proteins in different samples. In certain exemplary embodiments, the N-terminal (or C-terminal) peptides of two or more pro-

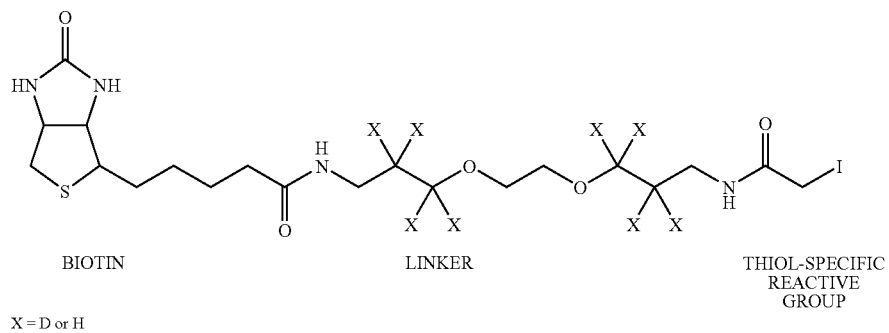

BIOTIN　　　　　　　　　LINKER　　　　　　　　　THIOL-SPECIFIC
　　　　　　　　　　　　　　　　　　　　　　　　　　REACTIVE
　　　　　　　　　　　　　　　　　　　　　　　　　　GROUP

X = D or H

Thus the stable isotopes are incorporated post isolation by selective alkylation of cysteines with a heavy (d8) or normal (d0) reagent. The two protein mixtures from different proteomic samples are then mixed, digested with trypsin and passed over a monomeric avidin-agarose column (avidin affinity chromatography). Because the ICAT label contains a biotin tag, ICAT-labeled (cysteine-containing) peptides are selectively isolated for analysis. Characterization and quantitation is accomplished by mass spectrometry copuled to a chromatogrphic technique (typically by microcapillary LC-electrospray ionization (ESI)-MS/MS). The ratio of ion intensities from co-eluting ICAT-labeled pairs permits the quantification, while a subsequent MS/MS scan allows protein identification.

While this approach substantially facilitates protein quantitation, ICAT has significant limitations. For example, it relies on specific labeling of cysteine residues and, although cysteine is present in most proteins (approximately 93%), proteins lacking cysteine residues cannot be detected by this method. Thus, not all proteins will be represented. In addition, although any given protein contains in average a relatively low number of cysteine residues, ICAT can and does produce multiple peptides for some proteins, which can complicate the analytical process. Thus, some proteins are represented multiple times. Therefore, unlike the present invention, the ICAT method cannot take advantage of the 1:1 stoichiometry of peptide to parent protein utilized in the present invention. Furthermore, the biotin-avidin binding can be subject to interference from sample matrices, and thus the avidin affinity chromatographic separation may be adversely affected. In addition, because the avidin/biotin binding is not 100% specific, the sample obtained after affinity chromatographic separation of the digest likely contains contaminants, which complicates the analytical process.

The present invention addresses several limitations of methods known in the art and provides a highly efficient method for quantitative determination of the relative amounts of proteins in different samples, while dramatically reducing teomic samples are differentially labeled by means of a detectable label, and the relative amounts of differentially labeled peptides are measured using a quantitative analytical method.

The detectable label referred to herein is taken to mean any group, entity or moiety that can be detected by quantitative analytical methods available in the art. Such quantitative analytical methods include but are not limited to, mass spectrometry, nuclear magnetic resonance spectroscopy (NMR), fluorescence spectroscopy, Uv-vis absorption spectroscopy and Fourier transform infra-red spectroscopy (FTIR). Selection of a detectable label suitable for analysis with any of these methods will be readily apparent to one skilled in the art. Preferably, each proteomic sample is independently labeled with different detectable labels. Optionally, the combined sample mixture is subjected to a separation step prior to analysis, effecting partial or complete separation of the differentially labeled peptides present in the mixture. Examples of separation techniques suitable for the practice of the invention are HPLC, gel electrophoresis, capillary electrophoresis, or other suitable chromatographic techniques. In one embodiment, the differentially labeled samples are combined and the differentially labeled N-terminal (or C-terminal) peptides are analyzed and quantitated together, so as to allow direct quantitation. Alternatively, the differentially labeled samples are analyzed separately: the N-terminal (or C-terminal) peptides in each differentially labeled peptide mixture are quantitated against a standard that is introduced in each peptide sample prior to analysis.

In certain exemplary embodiments, the N-terminal (or C-terminal) peptides of the invention are differentially isotopically labeled to generate pairs or sets of peptides that are substantially chemically identical, but which are distinguishable by mass. For example a pair of protecting group reagents, one of which is isotopically heavy and the other of which is isotopically light can be employed for the comparison of two samples, one of which may be a reference sample containing one or more known proteins in known amounts. For example, any one or more of the hydrogen, nitrogen, oxygen or sulfur atoms that may be present in the protecting group used in the terminal peptide selection method may be replaced with their isotopically stable isotopes (for example, $^2H$, $^{13}C$, $^{15}N$, $^{17}O$, $^{18}O$ or $^{34}S$). Differential isotopic labeling is preferably, but not necessarily, introduced into the peptides of this invention through the free carboxyl group of the N-terminal peptides. In another embodiment, differential isotopic labeling is introduced into the peptides of this invention through the free amino group of the C-terminal peptides.

In one embodiment, the quantitative methods described above are combined with a mass spectrometric technique for characterizing the N-terminally or C-terminally protected peptides and for identifying the proteins in the sample from which the N-terminally or C-terminally protected peptides were derived. Examples of suitable mass spectrometric techniques have been discussed above, and will be readily apparent to the person of ordinary skill in the art who wishes to practice the invention. In one embodiment the mass spectrometric technique is tandem mass spectrometry and the amino acid sequence of the N-terminally or C-terminally protected peptides is determined. In another embodiment, the mass spectrometric technique is coupled with a separation technique, such as HPLC, gel electrophoresis or CE, and the mixture of N-terminally or C-terminally protected peptides is subjected to a separation step prior to MS analysis. In an exemplary embodiment, the detectable labels in different samples are differentially isotopically labeled, and quantitative comparison of levels of N-terminally or C-terminally protected peptides (hence, the protein levels) in the different samples is effected by comparing the relative amounts of the differentially isotopically labeled labels in the different samples.

In an effort to more fully describe the state of the art to which the invention pertains, provided below are references relating to the application of mass spectrometric techniques to quantitative proteomics: Gygi S. P. et al., "Measuring gene expression by quantitative proteome analysis", *Curr Opin Biotechnol.*, 11 (4): 396-401, 2000; Mann M., "Quantitative proteomics?", *Nature Biotechnology*, 17:954-955, 1999; Hutchens et al., U.S. Pat. No. 6,225,047; and Waldman et al., Published U.S. Patent Application No. 2001/0039016.

One of ordinary skill in the art will recognize that the mass difference between differentially isotopically labeled peptides will depend on the isotopic mass difference among the selected detectable labels and the charge state of the peptides, which can be determined in the mass spectrometer itself based on the natural isotope distribution. When the mass spectrometer is coupled with a chromatographic separation technique, the differentially labeled peptide mixture is subjected to a separation step prior to mass analysis. The isotopic-related peptides essentially co-elute from the chromatographic unit (for example, HPLC) as they enter the MS ionization chamber. A given peptide appears as multiple peaks, due to each differentially labeled peptide (e.g., a doublet for two samples labeled differentially with methylamine-(d0) and methylamine-(d3)). In the MS spectrum, the peaks will be separated by an m/z equal to the difference in mass between the normal (d0) and heavy (d3) label present on the peptides. For example, when methylamine-(d0) and methylamine-(d3) are used to label the free carboxyl groups of N-terminally protected peptides in each sample, the peaks detected for the same peptide in differentially isotopically labeled samples will be separated by 3 m/z units. The relative intensity of the peaks in the set of multiple peaks (e.g., doublet) from the same peptide in differentially isotopically labeled samples directly reflects the relative concentrations of that peptide in the different samples. The underlying principle of this quantification method is that isotopically related peptides are chemically identical and therefore represent a perfect mutual internal standard. The intensities of the signals generated in the mass spectrometer from the differentially isotopically labeled peptides from different samples precisely reflect relative quantities of the peptide molecules present in those samples, respectively.

Differential Labeling of N- or C-terminal Peptides at the Free C- or N-termini, Respectively In certain embodiments, the inventive quantitative method comprises (i) providing two or more samples each containing one or more proteins; (ii) protecting, in each sample, the protein N- or C-termini with a suitable protecting agent; (iii) cleaving, in each sample, the terminally protected proteins with a suitable cleaving agent, thereby producing for each sample a mixture of terminally protected peptides and peptides comprising free amino and carboxyl groups corresponding to the cleavage sites; (iv) separating, for each sample, the terminally protected peptides from the peptide mixture, thereby reducing the sample complexity for each of the two or more protein samples to one terminal peptide per sample protein; (v) differentially labeling the terminally protected peptides of each sample with a suitable reagent comprising a detectable label, thereby generating two or more sets of differentially labeled terminal peptides; and (v) measuring relative levels of differentially labeled terminally protected peptides.

In one embodiment, the quantitation method of the invention uses the N-terminal peptide selection approach described herein, and comprises (i) providing two or more samples each containing one or more proteins; (ii) protecting, in each sample, the protein N-terminal amino groups with a suitable protecting agent; (iii) cleaving, in each sample, the N-terminally protected proteins with a suitable cleaving agent, thereby producing for each sample a mixture of N-terminally protected peptides and peptides comprising free amino and carboxyl groups corresponding to the cleavage sites; (iv) separating, for each sample, the N-terminally protected peptides from the peptide mixture, thereby reducing the sample complexity for each of the two or more protein samples to one N-terminal peptide per sample protein; (v) differentially labeling the N-terminally protected peptides of each sample with a suitable reagent comprising a detectable label, thereby generating two or more sets of differentially labeled N-terminal peptides; and (vi) measuring relative levels of differentially labeled N-terminally protected peptides.

In yet another embodiment, the method for quantitatively comparing protein levels in two or more samples relies on C-terminal peptides of the sample proteins for quantitation, and comprises (i) providing two or more samples each containing one or more proteins; (ii) protecting, in each sample, the protein C-terminal carboxyl groups with a suitable protecting agent; (iii) cleaving, in each sample, the C-terminally protected proteins with a suitable cleaving agent, thereby producing for each sample a mixture of C-terminally protected peptides and peptides comprising free amino and carboxyl groups corresponding to the cleavage sites; (iv) separating, for each sample, the C-terminally protected peptides from the peptide mixture, thereby reducing the sample complexity for each of the two or more protein samples to one C-terminal peptide per sample protein; (v) differentially labeling the C-terminally protected peptides of each sample with a suitable reagent comprising a detectable label, thereby generating two or more sets of differentially labeled C-terminal peptides; and (vi) measuring relative levels of differentially labeled C-terminally protected peptides.

In a variation of the above three embodiments, the sets of differentially labeled terminal peptides formed in step (iv) are combined prior to measuring the relative levels of differentially labeled terminally protected peptides.

It is to be understood that steps (ii)-(iv) in each of the above three embodiments can be carried out according to the N- or C-terminal peptide selection approach described herein. Thus specific starting materials, experimental conditions and general methodologies for protecting and cleaving the N-termini (or C-termini) of the sample proteins, and separating the resulting N-terminally (or C-terminally) protected peptides from the mixture will be readily apparent to the worker skilled in the art from the teachings of the N-terminal (or C-terminal) peptide selection method described herein.

In exemplary embodiments, the reagent comprising a detectable label is a carboxyl reactive group and reacts selectively in good yield to give a C-terminally labeled peptide that is stable to the projected reactions or experimental conditions. In other embodiments, the reagent comprising a detectable label is an amino reactive group and reacts selectively in good yield to give an N-terminally labeled peptide that is stable to the projected reactions or experimental conditions.

Preferably, but not necessarily, the labeled reagent has a minimum of additional functionality to avoid further sites of reaction. In certain embodiments, the labeled reagent is a carboxyl protecting agent. Examples of suitable carboxyl protecting agents are described elsewhere herein and will be readily apparent to one of ordinary skill in the art. For example, suitable protecting agents may include those that form carboxylic esters (for example, methanol or other lower aliphatic alcohol, diazomethane, MeI, $Me_3SiCHN_2$, $Me_2C(OMe)_2$, $CH_3OCH_2Cl$, $CH_3SCH_2Cl$, dihydropyran, $CH_3OCH_2CH_2OCH_2Cl$, $PhCH_2OCH_2Cl$, $Me_3SiCl$, $Et_3SiCl$, $Me_2PhSiCl$), amides (for example, methylamine, ethylamine, $Me_2NH$, pyrrolidine, piperidine) and hydrazide (for example, phenylhydrazine) derivatives, to name a few. Preferably, the carboxyl protecting agent is an aliphatic amine. In exemplary embodiments, functionalized of the free carboxyl group involves carbodiimide activation prior to reaction with a suitable protecting reagent (for example an aliphatic amine, such as methyl amine or ethylamine). In certain embodiments, the labeled reagent is an amine protecting agent. As discussed above, examples of suitable protecting groups include, but are not limited to, carbamates (including methyl, ethyl, tert-butyl (e.g., Boc) and 9-fluorenylmethyl carbamates (e.g., Fmoc), to name a few) amides, cyclic imide derivatives, N-Alkyl and N-Aryl amines, imine derivatives, and enamine derivatives, to name a few. In certain exemplary embodiments, the protecting agent is acetic anhydride, di-tert-butyl dicarbonate (i.e., Boc anhydride), 2-tert-butyloxy-carbonylamino -2-phenylacetonitrile (i.e., BOC—ON) or a 9-fluorenylmethoxy carbonyl reagent (i.e., Fmoc reagent) which generates a 9-fluorenylmethoxy carbamate upon reaction with a reactive free amine.

It will be appreciated that the present invention is not intended to be limited to the protecting agents described herein; rather, a variety of additional equivalent protecting groups can be readily identified using the above criteria and utilized in the present invention, as referenced herein.

In certain exemplary embodiments, the labeled reagent is available or can be prepared in different isotopic forms. For example, where the N-terminal peptide selection approach is used and labeling is intended at the peptide N-terminal free carboxyl groups, methylamine and methylamine-(d3) (or ethylamine and ethylamine-(d5)) can be used to differentially label the peptides. In one sample, the N-terminal peptide free carboxyl groups can be reacted with methylamine-(d0) under suitable conditions to generate the corresponding amide. In another sample, the N-terminal peptide free carboxyl groups can be reacted with methylamine-(d3) under suitable conditions to generate the corresponding deuteriated amide. Preferably, formation of the amides is accomplished through carbodiimide activation of the carboxyl group.

In other embodiments, where the C-terminal peptide selection approach is used and labeling is intended at the peptide C-terminal free amino groups, Boc anhydride-(d0) and BOC—ON-(d9), or acetic anhydride-(d0) and acetic anhydride-(d6) can be used to differentially label the peptides. For example, in one sample, the C-terminal peptide free amino groups can be reacted with BOC—ON-(d0) under suitable conditions to generate the corresponding carbamate. In another sample, the C-terminal peptide free amino groups can be reacted with BOC—ON-(d9) under suitable conditions to generate the corresponding deuteriated carbamate. In yet another embodiment, in one sample, the C-terminal peptide free amino groups can be reacted with acetic anhydride-(d0) under suitable conditions to generate the corresponding amide. In a second sample, the C-terminal peptide free amino groups can be reacted with acetic anhydride-(d6) under suitable conditions to generate the corresponding deuteriated amide.

It will be appreciated that the present invention is not intended to be limited to the differentially labeled protecting agents described herein; rather, a variety of additional equivalent protecting groups can be readily identified using the above criteria and utilized in the present invention.

Differential Labeling of Protein N- or C-termini

In another embodiment, the method for quantitatively comparing protein levels in two or more samples comprises (i) providing two or more samples each containing one or more proteins; (ii) differentially labeling each sample's protein N- or C-termini with a suitable protecting agent comprising a detectable label, thereby generating two or more sets of differentially labeled terminally protected proteins; (iii) cleaving the differentially labeled terminally protected proteins with a suitable cleaving agent, thereby producing two or more mixtures of differentially labeled terminally protected peptides and peptides comprising free amino and carboxyl groups corresponding to the cleavage sites; (iv) separating, for each of the two or more peptide mixtures, the differentially labeled terminally protected peptides from the non-terminally protected peptides, thereby effectively reducing the sample complexity to one differentially labeled terminal peptide per differentially labeled sample protein; and (v) measuring the relative levels of differentially labeled terminally protected peptides.

In a variation of the above embodiment, the sets of differentially labeled terminal peptides formed in step (ii) may be combined at any time prior to measuring the relative levels of differentially labeled terminally protected peptides.

In a certain exemplary variation of the same embodiment, the sets of differentially labeled terminal peptides formed in step (ii) are combined prior to the step of cleaving and the method comprises steps of: (i) providing two or more samples each containing one or more proteins; (ii) differentially labeling each sample's protein N- or C-termini with a suitable protecting agent comprising a detectable label, thereby generating two or more sets of differentially labeled terminally protected proteins; (iii) combining the sets of differentially labeled terminally protected proteins; (iv) cleaving the differentially labeled terminally protected proteins with a suitable cleaving agent, thereby producing a combined mixture of differentially labeled terminally protected peptides and peptides comprising free amino and carboxyl groups corresponding to the cleavage sites; (v) separating the differentially labeled terminally protected peptides from the non-terminally protected peptides, thereby reducing the sample complexity to one differentially labeled terminal peptide per differentially labeled sample protein; and (vi) measuring the relative levels of differentially labeled terminally protected peptides.

It is to be understood that all the steps prior to measuring the relative levels of differentially labeled terminally protected peptides in each of the above embodiment and recited variations thereof can be carried out according to the N- or C-terminal peptide selection approach described herein. Thus specific starting materials, experimental conditions and general methodologies for protecting and cleaving the protein N- or C-termini, and separating the resulting terminally protected peptides from the mixture will be readily apparent to the worker skilled in the art from the teachings of the terminal peptide selection approach described herein.

Whether differential labeling of terminal peptides at the free termini or differential labeling of protein termini (i.e., before enzymatic or chemical fragmentation) is used, combination of proteomic samples may be done any time after the step of differentially labeling the terminal peptides or proteins in each sample, but before measuring the relative levels of labeled peptides in the mixture. This ensures that each differentially labeled peptide pair/set is analyzed simultaneously, thus allowing relative quantitation (as opposed to absolute quantitation which necessitates the creation of a calibration curve). Preferably, when the protein labeling approach is used (e.g., differential labeling before enzymatic or chemical cleavage), the differentially labeled samples are combined immediately after the step of differentially labeling the protein samples. Thus the steps of cleaving the differentially labeled terminally protected proteins and separating the resulting differentially labeled peptides from the peptide mixture may be carried out simultaneously, with the combined samples.

In exemplary embodiments, where the N-terminal peptide selection approach is used, the protecting agent is an amine reactive group and reacts selectively in good yield to give a labeled N-terminally protected protein that is stable to the projected reactions or experimental conditions. In other embodiments, where the C-terminal peptide selection approach is used, the protecting agent is a carboxyl reactive group and reacts selectively in good yield to give a labeled C-terminally protected protein that is stable to the projected reactions or experimental conditions. Preferably, but not necessarily, the protecting agent has a minimum of additional functionality to avoid further sites of reaction.

In certain embodiments, the protecting agent is an amine protecting group. Examples of suitable amine protecting groups have been described above and will be readily apparent to one skilled in the art. In certain exemplary embodiments, the protecting agent is acetic anhydride, di-tert-butyl dicarbonate (i.e., Boc anhydride) or 9-fluorenylmethoxy carbonyl reagent (i.e., Fmoc reagent) which generates a 9-fluorenylmethoxy carbamate upon reaction with a reactive free amine. Examples of Fmoc reagents suitable for practicing the invention include, but are not limited to, Fmoc-Cl, Fmoc-$N_3$, Fmoc-OBt (Bt=benzotriazol-1-yl), Fmoc-OSu (Su=succinimidyl) and Fmoc-$OC_6F_5$. In other embodiments, the protecting agent is a carboxyl protecting group. Examples of suitable carboxyl protecting groups have been described above and will be readily apparent to one skilled in the art. In exemplary embodiments, functionalized of the free carboxyl group involves carbodiimide activation prior to reaction with a suitable protecting reagent (for example an aliphatic amine, such as methyl amine or ethylamine).

It will be appreciated that the present invention is not intended to be limited to the protecting agents described herein; rather, a variety of additional equivalent protecting groups can be readily identified using the above criteria and utilized in the present invention, as referenced herein.

In other exemplary embodiments, the protecting agents (for labeling the protein N- or C-termini) can be selected to carry differential isotopic labels that are useful for quantitative peptide analysis by mass spectrometry. Preferably, where the N-terminal peptide selection approach is used, the protecting agent is an amine protecting agent and it is available or can be prepared in different isotopic forms. Examples of amine protecting groups suitable for differentially isotopically labeling N-terminal peptides include 2-tert-butyloxy-carbonylamino-2-phenylacetonitrile-(d0) or -(d9) (i.e., BOC—ON-(d0) or -(d9)), acetyl chloride-(d0) or -(d3) and benzoyl chloride-(d0) or (d5), all available from ISOTEC, Miamisburg, Ohio, or acetic anhydride-(d0) or -(d6). For example, in one sample, the protein N-terminal free amino groups can be reacted with BOC—ON-(d0) under suitable conditions to generate the corresponding carbamate. In another sample, the protein N-terminal free amino groups can be reacted with BOC—ON-(d9) under suitable conditions to generate the corresponding deuteriated carbamate. Alternatively, the proteins in each sample can be differentially labeled by protecting the N-terminal amino groups with acetic anhydride-(d0) in one sample, and acetic anhydride-(d6) in another sample. As discussed previously herein, selective protection of the protein lysine residues may be preformed prior to N-terminal labeling. Lysine protection may be accomplished with a reagent such as O-methyl isouroea or O-methyl imidazole, generating trypsin cleavable protein samples.

In other embodiments, where the C-terminal peptide selection approach is used, the protecting agent is a carboxyl protecting agent and it is available or can be prepared in different isotopic forms. Examples of carboxyl protecting groups suitable for isotopically differentially labeling C-terminal peptides are aliphatic or alicyclic amines that are available in normal and heavy isotopic forms (for example, methylamine (d0 and d3) and ethylamine (d0 and d5)). For example, in one sample, the protein free carboxyl groups can be reacted with methylamine-(d0) under suitable conditions to generate the corresponding amide. In another sample, the protein free carboxyl groups can be reacted with methylamine-(d3) under suitable conditions to generate the corresponding deuteriated amide. Preferably, formation of the amides is accomplished through carbodiimide activation of the carboxyl group.

It will be appreciated that the present invention is not intended to be limited to the differentially isotopically labeled protecting agents described herein. Other stable isotopically labeled reagents, available from other chemical suppliers, will be readily apparent to the person of ordinary skill in the art who wants to practice the invention.

In one embodiment, differential labeling of the protein termini (N- or C-termini) provides information about which proteins are terminally blocked in the original proteomic sample. For example, where differential labeling of the protein N-termini is used, the N-terminal peptides not carrying the selected detectable label must have been blocked initially. Alternatively, where differential labeling of the protein C-termini is used, the absence of the selected detectable label on certain C-terminal peptides resulting from enzymatic or chemical cleavage of the proteomic samples indicates that those peptides (hence the corresponding original proteins) must have been blocked initially.

Preferably, where the desired terminal peptides are separated from the mixture by immobilization on a solid support either directly or indirectly through a linker, experimental release conditions will be such that selective release of the terminal peptides from the solid support occurs without cleavage of the labeled terminal protecting groups. For example, where differential labeling of the protein N-termini is used, the desired N-terminal peptides may be immobilized on a suitable solid support (hence separated from the rest of the peptide mixture) and subsequently released from the support. Upon release from the solid support, the N-terminal protecting groups carrying a suitable detectable label are retained on the peptides. Under such conditions, the N-terminal protecting agent can be used for differentially isotopic labeling for MS quantitation. A variety of amino or carboxyl protecting groups suitable for immobilization on various solid supports are available in the art. One of ordinary skill in the art can select a protecting reagent, optionally a linker, a solid support and release conditions that will allow retention of the protecting group at the peptide termini on release of the terminal peptides from the solid support material.

In general, there is no limit on the number of proteomic samples that may be quantitatively analyzed for differential protein expression and/or modification. In certain embodiments, the number of proteomic samples is 2 to 100, more preferably 2 to 25, even more preferably 2 to 10. In exemplary embodiments, quantitative proteomic analysis involves two samples.

The quantitative system of the invention allows a comparison of protein expression or modification in samples that are differentially affected by a change in condition or cell state. Such proteins may function as markers for the changed state and may provide a basis for "pharmacoproteomics" (e.g., identification of protein disease markers and protein drug targets and/or characterization of responses to pharmacological therapy). In one embodiment the system is for determining whether a protein is differentially present or modified between two different cells of different genetic backgrounds, tissue origins, and/or stages of development, including, for example, bacteria, yeast, plant, insect and mammal cells. In another embodiment one biological sample is derived from a healthy subject and another biological sample is from a subject suffering from a pathological condition. In one embodiment, one biological sample may derive from normal cells, and another biological sample is from transformed (e.g., cells that were not derived from a cancer but were produced by laboratory treatment of normal cells), diseased or genetically engineered cells (e.g., from site-directed mutation or gene knockout experiments). In one embodiment, the biological samples may be derived from cell previously exposed to different external stimuli (e.g., administration of a drug; contact with a potentially toxic material; change in nutrient level, temperature or passage of time). The sample can be selected from, for example, cell homogenates; cell fractions; biological fluids including urine, blood, and cerebrospinal fluid; tissue homogenates; tears; feces; saliva; mixtures of biological molecules including proteins, lipids, carbohydrates and nucleic acids generated by partial or complete fractionation of cell or tissue homogenates.

In certain embodiments, the proteomic sample is obtained by extracting proteins from a biological sample of interest. Preferably, the extraction method is such that little or no variation of protein expression is observed between multiple protein extraction runs of the same sample (e.g., protein extraction is preferably highly reproducible). Reproducibly in protein extraction methods is important where comparative differential protein expression and/or modification between two or more samples is to be evaluated since variations due to experimental protocols could either mask real differences in protein expression and/or modification or suggest false differences. Methods for extracting proteins from cells, for example, are well-known in the art and protein extraction according to these methods is sufficiently reproducible from sample to sample to allow meaningful analyses of differential protein expression/modification in two or more samples. For example, one of ordinary skill in the art could devise extraction methods or modify a known method to adapt it to a particular sample of interest from known methods to prepare protein samples for gel electroplhoresis or 2D SDS-PAGE, for example. See, for example, Bollag D. M. et al, "Protein Methods", Wiley-Liss Publishing, 1996; Walsh et al, ABRFnews, 9:11-21, 1998; Link et al, *Electrophoresis* 18:1314-1334, 1998; and Ducret et al, *Protein Sci.* 7:706-719, 1998, each of which is incorporated herein by reference to the extent that they are not inconsistent with the teachings of the invention.

In another aspect this invention provides a screening method for determining whether a test compound modulates protein expression or modification in a particular biological system. In one embodiment the method is for determining whether a test compound modulates the expression or modification of a protein in a biological sample, and the method further comprises a step of administering the test compound (e.g., a drug or a toxic agent) to a first biological sample but not to a second biological sample (control sample). A person of ordinary skill in the art will appreciate that the quantitative method of the invention is readily amenable to high-throughput assay format, and thus, the method could be used in combinatorial methods for drug discovery. Many compounds can be screened for their ability to affect protein expression according to the present invention. The method comprises quantitatively comparing protein levels in different proteomic samples obtained from biological systems exposed to different test compounds to that of a control sample (e.g., which has not been exposed to test compounds). A difference between the measured amount and the control amount indicates that the particular test compound modulates a particular protein expression pattern. Proteins that are found to be affected by exposure to certain test compounds are candidate diagnostic markers and/or drug targets. Proteins and peptides from any naturally-occurring environment or artificially-controlled environment can be assessed by the system herein.

Kits of the Invention

Another aspect of the present invention relates to kits useful for conveniently performing a method in accordance with the invention. To enhance the versatility of the subject invention, the reagents and or materials can be provided in packaged combination, in the same or separate containers, depending on the cross-reactivity and stability of the reagents and/or materials.

In one embodiment a kit, useful for identifying proteins in a proteomic sample, comprises: (i) one or more protecting agents for protecting protein N- or C-termini, and generating N- or C-terminally protected proteins; (ii) one or more cleaving agents for cleaving the terminally protected proteins into a mixture of terminally protected peptides and peptides comprising free amino and carboxyl groups; and (iii) means for separating the terminally protected peptides from the mixture.

In certain embodiments, the cleaving agents are chemical cleaving agents. In exemplary embodiments, the cleaving agents are enzymes for generating protein digests.

In certain embodiments, the kit of the invention further comprises a secondary amine protecting agent for selectively protecting the side chain lysine residues in the proteins. In an exemplary embodiment, the kit comprises O-methyl isosurea, O-methyl imidazole or their related chemical entities, or combination thereof.

In another embodiment, the kit comprises at least one amine protecting agent for N-terminally protecting proteins in the sample. In an exemplary embodiment, the kit comprises acetic anhydride, Boc anhydride, a Fmoc reagent, or combination thereof.

In yet another embodiment, at least one protecting agent is a carboxyl protecting agent and the kit comprises one or more carboxyl protecting agents for C-terminally protecting proteins in the sample. In a further embodiment, the kit comprises a reagent for activating protein carboxyl groups prior to protection. In one embodiment, the kit comprises a carbodiimide reagent. In one embodiment, the kit comprises one or more aliphatic or alicyclic amines for reacting with the protein carbodiimide-activated carboxyl groups. In an exemplary embodiment, the kit comprises methyl amine.

In one embodiment, at least one protecting agent is an amine protecting agent for N-terminally protecting proteins in the sample. In another embodiment, at least one protecting agent is a carboxyl protecting agent for C-terminally protecting proteins in the sample. In yet another embodiment, the protecting agent comprises a reactive group or a latent reactive group that can form a covalent bond with a solid support.

In another embodiment, the kit comprises a solid support for separating the desired terminally protected peptides from non-terminal peptides in the protein cleavage mixture. One or more solid supports may be provided with the kit, each being the same or different. In one embodiment, the solid support comprises reactive groups that can covalently bind to amines (for example for immobilizing non-N-terminally protected peptides). For example, the solid support may be a Br—, Cl—, carbonate-, CHO— or $CO_2H$-functionalized resin. In an exemplary embodiment, the solid support is a DITC-modified surface solid support. In another embodiment, the solid support comprises reactive groups that can covalently bind to carboxyl groups (for example for immobilizing non-C-terminally protected peptides). For example, the solid support may be a $NH_2$—, OH— or SH-functionalized resin. In an exemplary embodiment, the solid support reactive groups covalent bind to the carboxyl groups via a carbodiimide intermediate. In yet another embodiment, the solid support is for immobilizing terminally protected peptides and the solid support comprises reactive groups that can covalently bind to the protecting group present on the peptides.

In certain embodiments, the kit comprises a reagent for releasing immobilized peptides from the solid support, if desired. For example, where peptides are immobilized on the solid support through an amide linkage, the kit may comprise an anhydrous strong acid, such as trifluoro acetic acid (TFA), hydrochloric acid (HCl) or heptafluorobutanoic acid (HFBA).

In another embodiment, the kit comprises a linker for immobilizing terminally protected or non-terminally protected peptides on the solid support. The linker preferably comprises two reactive groups: one that can form a covalent bond with a pre-determined functionality on the peptides to be immobilized, another that can form a covalent bond with the reacting groups present on the solid support surface.

In yet another embodiment, a kit comprises: (i) one or more protecting agents which react with amine groups for protecting the protein N-termini; (ii) one or more protecting agents which react with carboxyl groups for protecting the protein C-termini; (iii) one or more cleaving agents for cleaving the N-terminally or C-terminally protected proteins into a mixture of N-terminally or C-terminally protected peptides and peptides comprising free amino and carboxyl groups; and (iv) means for separating the N-terminally or C-terminally protected peptides from the mixture.

In certain embodiments, the cleaving agents are enzymes for generating protein digests. In certain embodiments, the enzyme is trypsin, chymotrypsin, pepsin, papain, proline endopeptidase, staph protease, elastase, protease K, AspN, Lys-C, Arg-C or Glu-C. In an exemplary embodiment, the kit comprises trypsin.

In certain embodiments, the cleaving agents are chemical compounds for fragmenting proteins. In certain embodiments, the chemical compound is cyanogen bromide (CNBr), 2-nitro-5-thiocyanobenzoic acid, N-bromosuccinamide and other reactive halogen compounds, hydroxylamine, 1-2M formic or acetic acid, periodate oxidation, 2-(2-nitrophenyl-sulfenyl)-3-methyl-3-bromoindolenine or o-iodosobenzoic acid.

In yet another embodiment, the kits of the invention are useful for quantitative comparison of protein levels that are differentially present between two or more samples, and further comprise one or more reagents for differentially labeling the N-terminal and/or C-terminal peptides derived from proteins present in different samples.

In an exemplary embodiment, the reagents are differentially isotopically labeled and are used to covalently modify the free COOH group of N-terminally protected peptides and/or the free amino group of C-terminally protected peptides.

In one embodiment, the kits of the invention comprise an aliphatic or alicyclic amine in its normal and deuterated forms for selectively and differentially labeling the free carboxyl group of N-terminally protected peptides in different samples. In one exemplary embodiment, the aliphatic amine is methyl amine or ethylamine, and the kits of the invention comprise methylamine-(d0) and methylamine-(d3), or ethylamine(d0) and ethylamine-(d5). Preferably, the kits further comprise a carbodiimide reagent for activating the free carboxyl group prior to coupling with the aliphatic or alicyclic amine.

In another embodiment, the kits of the invention comprise a carbamate forming reagent in its normal and deuterated forms for selectively and differentially labeling the free amino group of C-terminally protected peptides in different samples as the corresponding carbamate moiety. In one exemplary embodiment, the carbamate forming reagent is 2-tert-butyloxy-carbonylamino-2-phenylacetonitrile (i.e., BOC—ON), and the kits of the invention comprise BOC—ON-(d0) and BOC—ON-(d9). In yet another embodiment, the kits of the invention comprise an amide forming agent in its normal and deuterated forms for selectively and differentially labeling the free amino group of C-terminally protected peptides in different samples as the corresponding amide moiety. In one exemplary embodiment, the amide forming reagent is acetic anhydride, and the kits of the invention comprise acetic anhydride-(d0) and acetic anhydride-(d6).

In another embodiment, the kits of the invention comprise one or more protecting agents for protecting the protein N-termini or C-termini in different samples and the protecting agents comprise differentially isotopically labeled detectable labels. Thus quantitative comparison of levels of N-terminally or C-terminally protected peptides (hence, levels of the corresponding proteins) in different samples is effected by comparing the relative amounts of the differentially isotopically labeled detectable labels in different samples.

In one embodiment, the kits of the invention comprise a carbamate forming reagent in its normal and deuterated forms for selectively and differentially labeling the protein N-terminal free amino groups in different samples as the corresponding carbamate moiety. In one exemplary embodiment, the carbamate forming reagent is 2-tert-butyloxy-carbonylamino-2-phenylacetonitrile (i.e., BOC—ON), and the kits of the invention comprise BOC—ON-(d0) and BOC—ON-(d9). In yet another embodiment, the kits of the invention comprise an amide forming agent in its normal and deuterated forms for selectively and differentially labeling the protein N-terminal free amino groups in different samples as the corresponding amide moiety. In one exemplary embodiment, the amide forming reagent is acetic anhydride, and the kits of the invention comprise acetic anhydride-(d0) and acetic anhydride-(d6).

In one embodiment, the kits of the invention comprise an aliphatic or alicyclic amine in its normal and deuterated forms for selectively and differentially labeling the protein C-terminal free carboxyl groups in different samples. In one exemplary embodiment, the aliphatic amine is methyl amine or ethylamine, and the kits of the invention comprise methylamine-(d0) and methylamine-(d3), or ethylamine(d0) and ethylamine-(d5). Preferably, the kits further comprise a carbodiimide reagent for activating the free carboxyl group prior to coupling with the aliphatic or alicyclic amine.

Equivalents

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance that can be adapted to the practice of this invention in its various embodiments and the equivalents thereof.

Exemplification

The practitioner has a well-established literature of peptide chemistry to draw upon, in combination with the information contained herein, for guidance on synthetic strategies, protecting groups, and other materials and methods useful for the preparation of the terminal peptides of this invention. Moreover, the practitioner is directed to the specific guidance and examples provided in this document relating to various exemplary methods for obtaining such terminal peptides and using them for protein identification and quantitation purposes. The methods of this invention can be understood further by the examples that illustrate some of the processes by which the inventive terminal peptides are prepared or used. It will be appreciated, however, that these examples do not limit the invention. Variations of the invention, now known or further developed, are considered to fall within the scope of the present invention as described herein and as hereinafter claimed.

According to the present invention, any available techniques can be used to make or prepare the terminal peptides of the invention. For example, a variety of solution phase synthetic methods such as those discussed in detail below may be used.

The starting materials and reagents used in preparing the terminal peptides of the invention are either available from commercial suppliers such as Aldrich Chemical Company (Milwaukee, Wis.), Bachem (Torrance, Calif.), Sigma (St. Louis, Mo.), or are prepared by methods well known to a person of ordinary skill in the art following procedures described in such references as Fieser and Fieser 1991, "Reagents for Organic Synthesis", vols 1-17, John Wiley and Sons, New York, N.Y., 1991; Rodd 1989 "Chemistry of Carbon Compounds", vols. 1-5 and supps, Elsevier Science Publishers, 1989; "Organic Reactions", vols 1-40, John Wiley and Sons, New York, N.Y., 1991; March 2001, "Advanced Organic Chemistry", 5th ed. John Wiley and Sons, New York, N.Y.; and Larock 1990, "Comprehensive Organic Transformations: A Guide to Functional Group Preparations", 2nd ed. VCH Publishers.

1. N-terminal Peptide Selection Approach—General Method

Protection of the $\epsilon$-lysine and arginine amino groups is achieved by treating a protein sample with O-methylisourea under suitable conditions (for example, reaction described in Beardsley et al., "Enhancing the intensities of lysine-terminated tryptic peptide ions in matrix-assisted laser desorption/ionization spectrometry", *Rapid Commun. Mass Spectrom.*, 14:2147-2153, 2000 may be adapted to a protein sample). The sample proteins are then N-terminally protected by reaction with a suitable protecting agent (e.g., acetic anhydride) under suitable conditions. The sample may be cleaned up at this stage. For example, excess lysine may be added to quench residual chemicals. The crude mixture may then be subjected to trypsin digestion thereby producing a mixture of N-terminally protected peptides and peptides comprising free amino and carboxyl groups corresponding to the cleavage sites. The peptide mixture may then be passed onto a DITC-modified solid support, which captures moieties bearing reactive free amines (alternatively, a gluteraldehyde-modified surface may be used), thereby effecting immobilization of the non-N-terminally protected peptide fragments in the mixture. Upon washing the solid support, the desired N-terminally protected peptides may be collected and analyzed by MS, preferably tandem MS. The peptides are fragmented and their MS fragmentation patterns are used to screen available databases to determine the amino acid sequence of the terminal peptides. The amino acid sequence information may then be used to screen protein databases to identify the parent proteins from which the terminal peptides may be derived.

2. One Embodiment of the N-terminal Peptide Selection Approach

In a exemplary embodiment, a protein sample is obtained from a biological sample. The sample is treated with 100-1000 molar excess of O-methylisourea in $H_2O$ at pH 9, 50° C. for 2 hours, thereby selectively protecting the protein lysine residues in the sample and producing a trypsin cleavable protein mixture (the reaction mixture may be adjusted to pH 9 by addition of ammonium hydroxide). Protection of the protein N-terminal free amino groups is accomplished by reacting with an excess acetic anhydride (e.g., 10-100 molar excess) in $H_2O$ at pH 9, 50° C. for 2 hours. The sample is then subjected to trypsin digestion by reacting the N-terminally protected protein mixture with a trypsin solution buffered to pH 7.5 at 37° C. for 15 hours. For example, a 1:20 w/w enzyme/substrate ratio may be used (e.g., 1 µg trypsin and 20 µg proteins). The resulting peptide mixture is then exposed to a DITC-modified solid support, thereby effecting immobilization of peptides carrying a free and reactive N-terminal on the solid surface. After sufficient washing of the surface with a suitable solvent (e.g., H₂O/AcCN/AcOH v/v 50/50/0.2), the desired N-terminally protected peptides are collected in the wash solvent. The solvent fractions containing the desired N-terminal peptides may be lyophilized (e.g., on speedvac). Alternatively, the fractions may be concentrated on a reverse-phase chromatography column. The peptide residue is analyzed by LC/MS. The peptides are fragmented and their MS fragmentation patterns are used to screen available databases to determine the amino acid sequence of the terminal peptides. The amino acid sequence information may then be used to screen protein databases to identify the parent proteins from which the terminal peptides may be derived.

3. Comparative Differential Protein Expression in Two Proteomic Samples Using the Inventive N-terminal Peptide Selection Approach—Differential Isotopic Labeling Prior to Protein Enzymatic Cleavage.

In a exemplary embodiment, protein samples are obtained from two cell states (e.g., diseased vs. normal cell or stressed vs. normal cell). Each sample is treated with 100-1000 molar excess of O-methylisourea in H₂O at pH 9, 50° C. for 2 hours, thereby selectively protecting the protein lysine residues and producing two trypsin cleavable protein mixtures (the reaction mixture may be adjusted to pH 9 by addition of ammonium hydroxide). In one sample, protein N-termini are protected with acetic anhydride-d(0) (alternatively BOC—ON-(d0) can be used) under suitable conditions. In the second sample, protein N-termini are protected with BOC—ON-(d9) under suitable conditions. For example, suitable reaction conditions for protection of the protein N-terminal free amino groups in each sample include reacting with an excess acetic anhydride-d(0) or -d(6) (e.g., 10-100 molar excess) in H₂O at pH 9, 50° C. for 2 hours. The resulting samples are combined, and the combined sample is then subjected to trypsin digestion (e.g., reaction with a trypsin solution buffered to pH 7,5 at 37° C. for 15 hours). The resulting peptide mixture is then exposed to a DITC-modified solid support, thereby effecting immobilization of peptides carrying a free and reactive N-terminal on the solid surface. After sufficient washing of the DITC-modified surface with a suitable solvent (e.g., H₂O/AcCN/AcOH v/v 50/50/0.2), the desired differentially isotopically labeled N-terminal peptides are collected in the washes. If desired, The solvent fractions containing the desired N-terminal peptides may be separately lyophilized; e.g., on speedvac (Alternatively, the fractions may be separately concentrated on a reverse-phase chromatography column). An aliquot is analyzed by LC/MS and the differential amounts of proteins in the original samples can be determined by measuring the relative amounts of each differentially isotopically labeled peptide in the mixture. If tandem MS is used, the amino acid sequence of each peptide in the mixture can be determined, and the identity of the corresponding protein in the original samples can be established by database searching.

4. Comparative Differential Protein Expression in Two Proteomic Samples Using the Inventive N-terminal Peptide Selection Approach—Differential Isotopic Labeling after Protein Enzymatic Cleavage.

In a exemplary embodiment, protein samples are obtained from two cell states (e.g., diseased vs. normal cell or stressed vs. normal cell). Each sample is treated with 100-1000 molar excess of O-methylisourea in H₂O at pH 9, 50° C. for 2 hours, thereby selectively protecting the protein lysine residues and producing two trypsin cleavable protein mixtures (the reaction mixture may be adjusted to pH 9 by addition of ammonium hydroxide). For each sample, protection of the protein N-terminal free amino groups is accomplished by reacting with an excess acetic anhydride (e.g., 10-100 molar excess) in H₂O at pH 9, 50° C. for 2 hours. Each sample is then subjected to trypsin digestion by reacting each N-terminally protected protein mixture with a trypsin solution buffered to pH 7.5 at 37° C. for 15 hours, thereby producing two peptide mixtures. Each resulting peptide mixture is then separately exposed to a DITC-modified solid support, thereby effecting immobilization of peptides carrying a free and reactive N-terminal on the solid surface. After sufficient washing of each DITC-modified surface with a suitable solvent (e.g., H₂O/AcCN/AcOH v/v 50/50/0.2), the desired N-terminally protected peptides are collected in the washes, separately for each sample. The solvent fractions containing the desired N-terminal peptides may be separately lyophilized (e.g., on speedvac). Alternatively, the fractions may be separately concentrated on a reverse-phase chromatography column. In one sample, the peptide free C-termini are activated with a suitable carbodiimide reagent and subsequently reacted with methylamine-(d0). In the second sample, the peptide free C-termini are activated with a suitable carbodiimide reagent and subsequently reacted with methylamine-(d3). The samples are then combined, and the resulting mixture of differentially isotopically labeled peptides is analyzed by LC/MS. The differential amounts of proteins in the original samples can be determined by measuring the relative amounts of each differentially isotopically labeled peptide in the mixture. If tandem MS is used, the amino acid sequence of each peptide in the mixture can be determined, and the identity of the corresponding protein in the original samples can be established by database searching.

What is claimed is:

1. A mass spectroscopic method for comparing protein levels in two or more samples comprising steps of:
   a. labeling the N- or C-terminus of proteins in a first protein sample with a first detectable isotopic label to generate a first labeled protein sample comprising a first set of labeled proteins;
   b. labeling the proteins of a second protein sample at said terminus with a second detectable isotopic label to generate a second labeled protein sample comprising a second set of labeled proteins, wherein the second detectable isotopic label is distinguishable from the first detectable isotopic label;
   c. cleaving the proteins of the first and second sets of labeled proteins with a cleaving agent, thereby producing a mixture comprising isotopically labeled proteins and non-labeled peptides;
   d. separating the isotopically labeled proteins from the non-labeled peptides;
   e. measuring the level of the isotopically labeled proteins in each sample by a mass spectroscopic technique; and
   f. comparing levels of the isotopically labeled proteins in the first and second samples.

2. The method of claim 1, wherein the first and second detectable isotopic labels are differentially labeled protecting group reagents wherein one protecting group reagent is isotopically heavy and the other protecting group reagent is isotopically light.

3. The method of claim 2, wherein the isotopically heavy protecting group reagent is comprises an isotope selected from the group consisting of $^2H$, $^{13}C$, $^{15}N$, $^{17}O$, $^{18}O$ and $^{34}S$.

4. The method of claim 2, wherein the isotopically heavy protecting group reagent comprises deuterium.

5. The method of claim 2, wherein the labeling comprises reacting the differentially labeled protecting group reagents with a free carboxyl group of the C-termini.

6. The method of claim 5 further comprising activating the free carboxyl group of the C-termini with carbodiimide.

7. The method of claim 6, wherein the differentially labeled protecting group comprises an aliphatic or alicyclic amine.

8. The method of claim 6, wherein the differentially labeled protecting group comprises methylamine, methylamine-(d3), ethylamine or ethylamine-(d5).

9. The method of claim 2, wherein the labeling comprises reacting the differentially labeled protecting group reagents with the free amino group of the N-termini.

10. The method of claim 9 further comprising reacting the differentially labeled protecting group reagents with the free amino group of the N-termini to form amide moieties.

11. The method of claim 10, wherein the differentially labeled protecting group reagents comprise anhydrides.

12. The method of claim 10, wherein the differentially labeled protecting group reagents comprise acetic anhydride, acetyl chloride, benzoyl chloride, di-tert-butyl dicarbonate (Boc anhydride), 2-tert-butyloxy-carbonylamino-2-phenylacetonitrile (BOC—ON), 9-fluorenylmethoxy carbonyl (Fmoc), Fmoc-Cl, Fmoc-$N_3$, Fmoc-OBt, Fmoc-OSu, Fmoc-$OC_6F_5$, or isotopically substituted forms thereof.

13. The method of claim 10, wherein the differentially labeled protecting group reagents comprise acetic anhydride-d(0) and acetic anhydride-d(6).

14. The method of claim 1 further comprising mixing the differentially isotopically labeled proteins together prior to measuring.

15. The method of claim 1, wherein the samples are proteomic samples.

16. The method of claim 1, wherein the proteins comprise peptides.

17. The method of claim 1, wherein the measuring comprises a mass spectrometric technique coupled to a separation technique.

18. The method of claim 17, wherein the separation technique comprises HPLC, gel electrophoresis or capillary electrophoresis.

19. The method of claim 17, wherein the comparison step is performed by using a mass spectrometric technique that produces signals that includes multiple peaks separated by an m/z equal to the difference in mass between a differentially isotopically labeled protein.

20. The method of claim 1, wherein one or more proteins comprise amino or carboxyl side chain groups; and
    further comprising selectively protecting the amino or carboxyl side chain groups with a protecting agent.

21. The method of claim 20, wherein the protecting agent is O-methyl isourea or O-methyl imidazole.

* * * * *